United States Patent [19]

Shudo et al.

[11] Patent Number: 5,652,232

[45] Date of Patent: Jul. 29, 1997

[54] BENZOLACTAM DERIVATIVES

[75] Inventors: Koichi Shudo, 9-18, Shimo-takaido 5-chome, Suginami-ku, Tokyo; Yasuyuki Endo, Chiba; Tamio Fujiwara, Hyogo; Akihiko Sato, Osaka, all of Japan

[73] Assignees: Shionogi & Co., Ltd., Osaka; Koichi Shudo, Tokyo, both of Japan

[21] Appl. No.: 615,286

[22] PCT Filed: Sep. 22, 1994

[86] PCT No.: PCT/JP94/01561

§ 371 Date: May 24, 1996

§ 102(e) Date: May 24, 1996

[87] PCT Pub. No.: WO95/09160

PCT Pub. Date: Apr. 6, 1995

[30] Foreign Application Priority Data

Sep. 30, 1993 [JP] Japan ................................. 5-268074

[51] Int. Cl.⁶ ...................... A61K 31/395; C07D 245/06
[52] U.S. Cl. .............................................. 514/183; 540/460
[58] Field of Search ............................. 540/460; 514/183

[56] References Cited

FOREIGN PATENT DOCUMENTS

| 0491218 | 6/1992 | European Pat. Off. ............... 540/460 |
| 4-275287 | 9/1992 | Japan ..................................... 540/460 |

OTHER PUBLICATIONS

Kogan et al., "A Regio–and Stereocontrolled Total Synthesis of (−)–Indolactam–V", *Tetrahedron*, 46, pp. 6623–6632 (1990).

International Search Report (in Japanese and in English).

International Preliminary Examination Report (in Japanese and in English).

Kozikowski et al., "Synthesis, Molecular Modeling, 2–D NMR, and Biological Evaluation of ILV Mimics as Potential Modulators of Protein Kinase C", *J. Am. Chem. Soc.*, 115, pp. 3957–3965 (1993).

*Primary Examiner*—Robert T. Bond
*Attorney, Agent, or Firm*—Greenblum & Bernstein, P.L.C.

[57] ABSTRACT

A benzolactam derivative represented by the following formula (I):

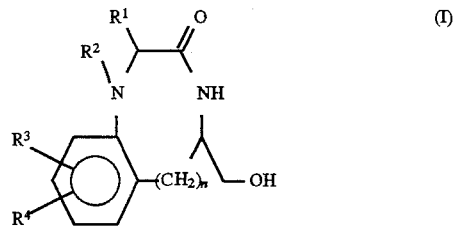

wherein n represents an integer of from 1 to 3; $R^1$ represents a straight- or branched-chain alkyl group or an aralkyl group; $R^2$ represents a straight- or branched-chain alkyl group; $R^3$ and $R^4$ independently represent a hydrogen atom or a straight- or branched-chain alkyl group, and when $R^3$ and $R^4$ are adjacent each other on the phenyl group, they may be combined to form a cycloalkyl ring together with two carbon atoms of the phenyl group to which $R^3$ and $R^4$ bind, and said cycloalkyl ring may optionally have one or more substituents; and a anti-retroviral agent comprising the same as an active ingredient.

9 Claims, No Drawings

BENZOLACTAM DERIVATIVES

FIELD OF ART

The present invention relates to benzolactam derivatives. More specifically, the present invention relates to benzolactam derivatives having anti-human acquired immunodeficiency syndrome virus activity and useful for the preventive and therapeutic treatment of AIDS.

BACKGROUND ART

AIDS (acquired immuno-deficiency syndrome) is a disease caused by an infection of one of retroviruses, human acquired immuno-deficiency virus (HIV). Any effective therapeutic method for treatment of the infection of the human acquired immuno-deficiency virus has not yet been developed, and the spread of AIDS has become a worldwide serious problem. Azidodeoxythymidine (AZT), dideoxyinosine (DDI), and dideoxycytosine (DDC) have been developed to date as anti-retroviral drugs having inhibitory activities against reverse transcriptions by retroviruses, which are used for the therapeutic treatment of AIDS. However, these drugs induce severe side effects such as cytotoxicities and their clinical applications are limited.

In addition, appearances of resistant strains having resistances against these drugs have also been problems. Therefore, developments of medicament having potent anti-retroviral activity and reduced side effects are much desired.

An object of the present invention is thus to provide novel substances which have excellent inhibitory activities against retroviruses and are useful as anti-retroviral drug with reduced side effects such as cytotoxicity.

DESCRIPTION OF THE INVENTION

The inventors of the present invention conducted various studies to achieve the foregoing object, and as a result, they found that the novel benzolactam derivatives according to the present invention had excellent inhibitory activities against retroviruses and reduced side effects such as cytotoxicity. They also found that the derivatives were useful for the treatment and prevention of AIDS. The present invention was achieved on the basis of these findings.

The present invention thus provides benzolactam derivatives represented by the following formula (I).

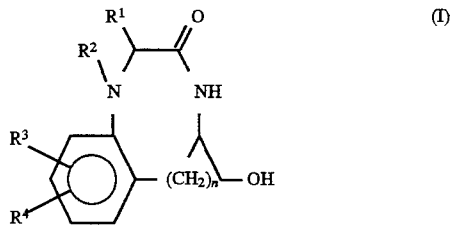

According to another aspect of the present invention, anti-retroviral drugs comprising the benzolactam derivative represented by the above formula (I) as an active ingredient are provided.

The benzolactam derivatives of the present invention have in their ring structures nitrogen atoms directly bound to the phenyl ring (nitrogen atom at the 1-position in the benzolactam ring), and in that regard they are structurally distinguishable from the compounds 4a–c and 14a disclosed in J. Am. Chem. Soc., 115, pp.3957–3965, 1993. In addition, the above-mentioned publication does not disclose that the compounds 4a–c and 14a have anti-retroviral activity.

BEST MODE FOR CARRYING OUT THE INVENTION

In the formula (I), n represents an integer of from 1 to 3, preferably an integer of 1 or 2. $R^1$ represents a straight- or branched-chain alkyl group or an aralkyl group. Examples of the alkyl group include, for example, straight- or branched-chain alkyl groups containing 1 to 12 carbon atoms. For example, lower alkyl groups such as isopropyl group, isobutyl group, or t-butyl group, and alkyl groups containing 8 to 10 carbon atoms such as n-octyl group, n-nonyl group, or n-decanyl group may preferably be used. Examples of the aralkyl group include, for example, lower aralkyl groups such as benzyl group and phenethyl group. The carbon atom to which $R^1$ binds (the carbon atom at the 2-position in the benzolactam ring) is an asymmetric carbon, on which two configurations are possible in respect of $R^1$. Assuming that the 8- to 10-membered ring structure is a plane in the chemical structure represented by the above general formula (I), $R^1$ may be either in the configuration being upward or downward from the plane. Both of these stereoisomers fall within the scope of the present invention. Similarly, the carbon atom which is adjacent to the nitrogen atom of the amide group (—NH—CO—) in the 8- to 10-membered ring and is substituted with the hydroxymethyl group (—CH$_2$OH) (the carbon atom at the 5-position in the benzolactam ring) is also an asymmetric carbon. Therefore, the hydroxymethyl group may be either in the configuration being upward or downward from the plane assuming that the 8- to 10-membered ring structure is a plane in the chemical structure represented by the above general formula (I). Both of such stereoisomers fall within the scope of the present invention. In addition, any mixtures of these stereoisomers fall within the scope of the present invention. Assuming that the 8- to 10-membered ring structure is a plane in the chemical structure represented by the above general formula (I), the compounds whose $R^1$ and the hydroxymethyl group bound to the carbon atom at the 5-position are over the same side of the plane may sometimes be referred to as epimers.

$R^2$ represents a straight- or branched-chain alkyl group. For example, straight- or branched-chain alkyl groups having from 1 to 12 carbon atoms may be used. Lower alkyl groups such as methyl group or ethyl group are preferred, and methyl group is most preferred. In addition, alkyl groups such as those having 8 to 12 carbon atoms are preferred as $R^2$, where $R^1$ is a lower alkyl group such as isopropyl group, isobutyl group, or t-butyl group, and where both of substituents represented by $R^3$ and $R^4$ are hydrogen atoms, or alternatively, either or both of them are lower alkyl groups. Examples of such groups include, for example, n-octyl group, n-nonyl group and n-decanyl group.

$R^3$ and $R^4$ independently represent a hydrogen atom or a straight- or blanched-chain alkyl group. Examples of the alkyl groups include, for example, straight- or branched-chain alkyl groups having 1 to 12 carbon atoms, and alkyl groups having 8 to 12 carbon atoms are preferred. Normal decanyl group is particularly preferred. $R^4$ is preferably a hydrogen atom where $R^3$ is an alkyl group having 8 to 12 carbon atoms. In that case, the positions of substitution by the alkyl group having 8 to 12 carbon atoms as $R^3$ are not particularly limited. For example, assuming that the nitrogen atom at the 1-position of the benzolactam ring is an amino group on the phenyl ring, $R^3$ is preferably placed at the m- or p-position of the amino group. Compounds where both of $R^3$ and $R^4$ are hydrogen atoms are also preferred.

In addition, where $R^3$ and $R^4$ are adjacent each other on the phenyl group, they may be combined to form a cycloalkyl ring together with two carbon atoms of the phenyl group on which $R^3$ and $R^4$ are attached. The cycloalkyl may preferably be a 5- to 7-membered ring, and particularly preferably a 6-membered ring. The cycloalkyl ring may be substituted with one or more lower alkyl groups. An example of such alkyl groups includes methyl group. For example, the two carbon atoms consisting the cycloalkyl ring adjacent each other and directly attached to the phenyl ring, may be substituted by four methyl groups.

Among the compounds of the present invention represented by the formula (I), preferred compounds include those listed in the following Table 1 and shown by chemical structures. However, the scope of the present invention is not limited to those compounds.

TABLE 1

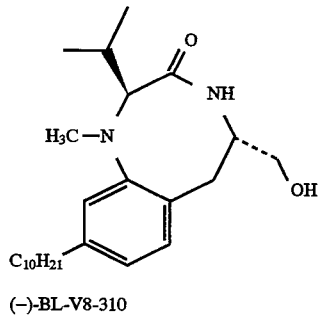

| Compound | n | $R^1$ | $R^2$ | $R^3$ | $R^4$ |
|---|---|---|---|---|---|
| BL-V8 | 1 | $-CH(CH_3)_2$ | $-CH_3$ | $-n-C_{10}H_{21}$ | H |
| BL-V8-310 | 1 | $-CH(CH_3)_2$ | $-CH_3$ | H | H |
| BL-V8-23T | 1 | $-CH(CH_3)_2$ | $-CH_3$ | $-C(CH_3)_2CH_2CH_2C(CH_3)_2-$ | |
| BL-V9 | 2 | $-CH(CH_3)_2$ | $-CH_3$ | $-n-C_{10}H_{21}$ | H |
| BL-V9-310 | 2 | $-CH(CH_3)_2$ | $-CH_3$ | H | H |
| BL-V9-23T | 2 | $-CH(CH_3)_2$ | $-CH_3$ | $-C(CH_3)_2CH_2CH_2C(CH_3)_2-$ | |
| BL-V10 | 3 | $-CH(CH_3)_2$ | $-CH_3$ | $-n-C_{10}H_{21}$ | H |
| BL-V10-310 | 3 | $-CH(CH_3)_2$ | $-CH_3$ | H | H |
| BL-V10-23T | 3 | $-CH(CH_3)_2$ | $-CH_3$ | $-C(CH_3)_2CH_2CH_2C(CH_3)_2-$ | |
| BL-V8-C10 | 1 | $-n-C_{10}H_{21}$ | $-CH_3$ | H | H |
| BL-V8-N10 | 1 | $-CH(CH_3)_2$ | $-n-C_{10}H_{21}$ | H | H |

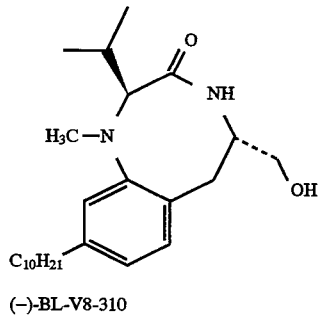

(−)-BL-V8-310

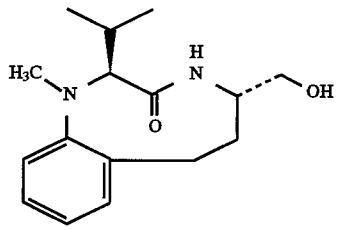

BL-V9

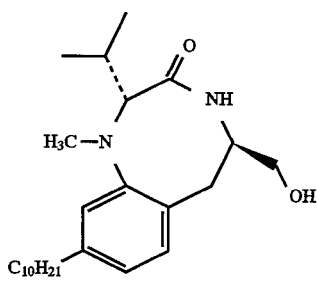

(+)-BL-V8-310

TABLE 1-continued

Compound of formula (1) with substituents R¹, R², R³, R⁴ and (CH₂)ₙ-OH chain, NH-C(=O) linkage to aromatic ring bearing NR²R¹ group.

| Compound | n | R¹ | R² | R³ | R⁴ |
|----------|---|-----|-----|-----|-----| epi-BL-V9

(−)-epi-BL-V8-310

BL-V9-310

(+)-epi-BL-V8-310

TABLE 1-continued

Structure (1):

Compound | n | R¹ | R² | R³ | R⁴ epi-BL-V9-310

Examples of preparation methods for the benzolactam derivatives of the present invention are shown in the schemes below in reference to the compound of the above general formula wherein n=1; $R^1$=—$CH(CH_3)_2$; $R^2$=—$CH_3$; $R^3$=n-$C_{10}H_{21}$; $R^4$=H (BL-V8-310) and the compound where n=2; $R^1$=—$CH(CH_3)_2$; $R^2$=—$CH_3$; $R^3$=n-$C_{10}H_{21}$; $R^4$=H (BL-V9-310). However, the compounds of the present invention and the method for preparing thereof are not limited to these preparation examples. Detailed explanations about the preparations of the above compounds and other compounds are also given in Examples of the specification.

Reaction conditions in the schemes are as follows:

a) $C_3CONHCH(COOC_2H_5)_2$, NaH/DMF;

b) $C_9H_{19}P^+Ph_3Br^-$, n-BuLi/THF;

c) HCl/AcOH; d) $SOCl_2$/EtOH; e) $Boc_2O/CH_2Cl_2$; f) $LiBH_4$/THF;

g) $H_2$, Pd-C/EtOH; h) HCOOH, AcOH; i) $BH_3$/THF;

j) Triflate of benzyl DL-α-hydroxyisovalerate, 2,6-lutidine/$CH_2Cl_2$;

k) N-hydroxysuccinimide, DCC/$CH_3CN$;

l) $CF_3COOH/CH_2Cl_2$; m) aq. $NaHCO_3/CH_3COOEt$;

n) $OHCH_2CH_2OH$, TsOH/toluene; o) $PPh_3$/toluene;

p) $K_2CO_3$/DMF;

q) Pyridinium p-toluenesulphonate/acetone, $H_2O$

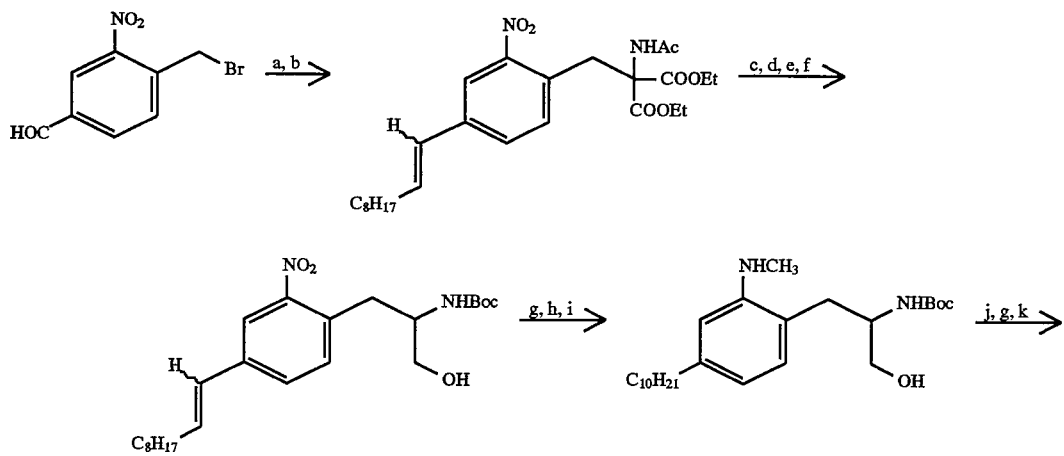

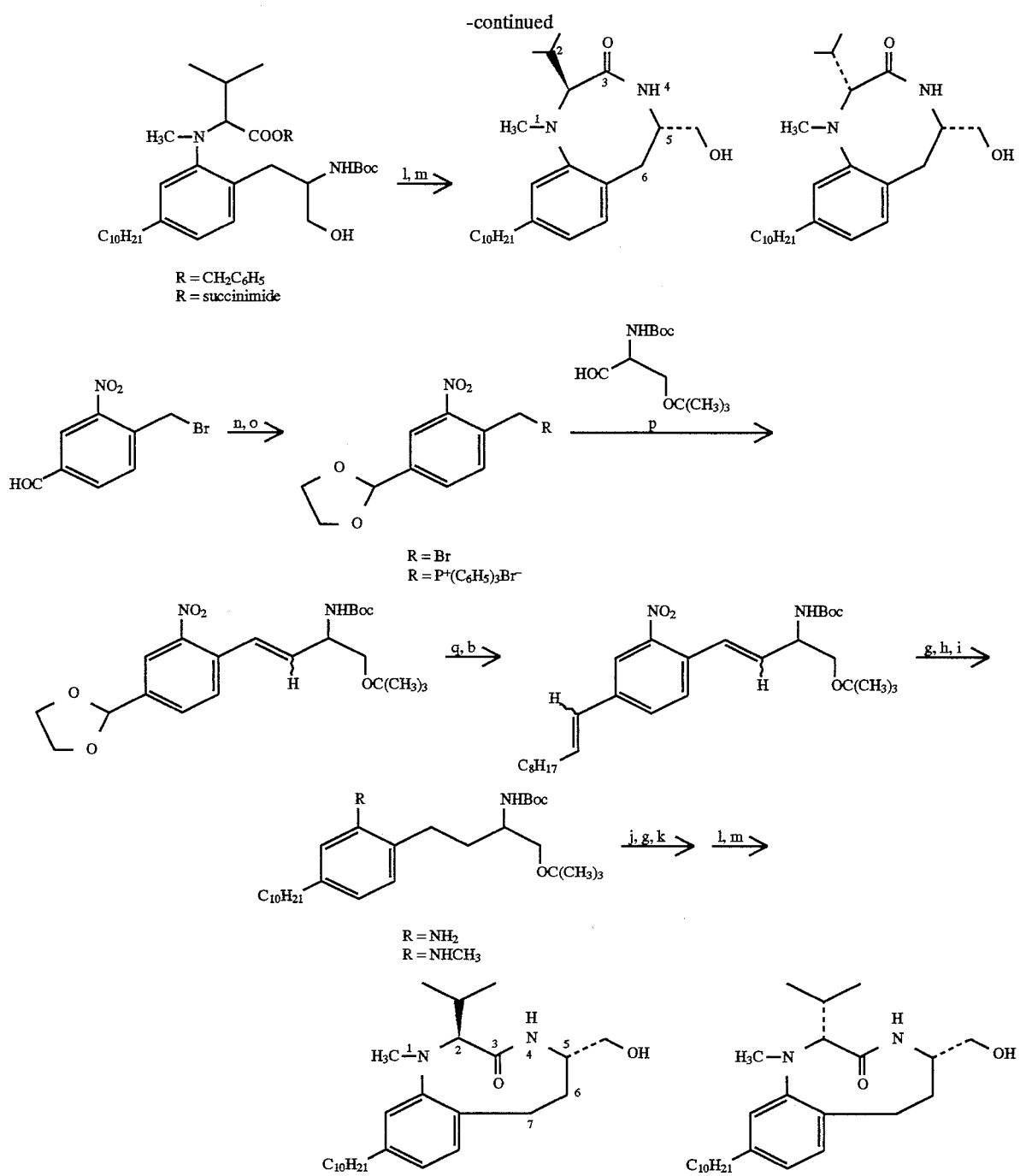

The benzolactam derivatives of the present invention have excellent anti-retroviral activity and reduced side effects such as cytotoxicity. Accordingly, retroviral agents comprising the benzolactam derivatives of the present invention as an active ingredient are useful for preventive and therapeutic treatments of retroviral infectious diseases such as AIDS.

The compounds of the formula (I), per se, may be used as the anti-retroviral agents of the present invention. Where the anti-retroviral agents of the present invention are administered orally or parenterally to mammals including human beings for therapeutic and/or preventive treatments of diseases such as AIDS, it is preferred to administer a pharmaceutical composition manufactured by adding pharmacologically and pharmaceutically acceptable additives to the compound of the formula (I). Such pharmaceutical compositions may be chosen by a person ordinarily skilled in the art depending on the purposes and methods of treatments. Examples of orally administrable pharmaceutical compositions include, for example, powder, tablets, granules, subtilized granules, solutions, and syrups. Examples of pharmaceutical compositions suitable for parenteral administration include, for example, injections, drip infusions, external preparations, suppositories, nasal drops, and ear drops.

For pharmaceutical compositions suitable for oral, percutaneous, or transmucosal administration, pharmacologically and pharmaceutically acceptable additives, for example, excipients, for example, glucose, lactose, D-mannitol, starch, and crystalline cellulose; disintegrators or disintegrating accelerators, for example, carboxymethylcellulose, starch, and carboxymethylcellulose calcium; binders, for example, hydroxypropylcellulose, hydroxypropylmethylcellulose, polyvinylpyrrolidone, and gelatine; lubricants, for example, magnesium stearate and talc; coating agents, for example, hydroxypropylmethylcellulose, saccharose, polyethylene glycol, and titanium oxide; base materials, for example, vaseline, liquid paraffin, polyethylene glycol, gelatine, kaolin, glycerin, purified water, and hard fat; propellants, for example, flons, diethyl ether, and compressed gases; adhesives, for example, sodium polyacrylate, polyvinyl alcohol, methylcellulose, polyisobutylene, and polybutene; and base cloths, for example, cotton cloth and plastic sheets, may be used.

For pharmaceutical compositions suitable as injections or drip infusions, pharmaceutical additives, for example, dissolving agents or dissolving accelerators which provide aqueous injections or injections dissolved before using, for example, distilled water for injection, physiological saline, and propylene glycol; isotonic agents, for example, glucose, sodium chloride, D-mannitol, and glycerin; pH adjusting agents, for example, inorganic acids, organic acids, inorganic bases, and organic bases, may be used.

Doses of the retroviral agents of the present invention can be appropriately chosen by a person ordinarily skilled in the art depending on, for example, a type of retroviral infectious disease to be prevented or treated, or age and conditions of a patient. Generally, a dose for an adult may be from about 0.1 to 100 mg per day.

EXAMPLES

The present invention will be more specifically explained by Examples. However, the scope of the present invention is not limited to these examples.

Example 1

Preparation of (±)-BL-V8-310 and (±)-epi-BL-V8-310

Terephthalaldehyde (25.0 g) was suspended in water (20 ml) and ethanol (80 ml). Pd/C (220 mg) was added to the suspension and then hydrogen gas (4.3 l) was introduced. The catalyst was removed by filtration and the filtrate was concentrated to give p-hydroxymethylbenzaldehyde (25.2 g). The product was dissolved in toluene (100 ml) and 48% HBr (50 ml) and the solution was refluxed for 2 hours. The reaction mixture was poured into iced water and the mixture was extracted with ethyl acetate. The organic layer was washed successively with water and saturated saline and dried, and then the solvent was removed by evaporation under reduced pressure. The residue was recrystallized from n-hexane to give colorless needles (37.5 g, yield: 82%). mp 97.5°–98.0° C.

Elemental Analysis: $C_8H_7OBr$ Calculated N: 0.00%; C: 48.27%; H: 3.54% Found N: 0.00%; C: 48.19%; H: 3.49%

$KNO_3$ (11.65 g) was added to concentrated sulfuric acid (200 ml) at 0° C. and the mixture was stirred for 1 hour. The above-obtained obtained bromo compound (22.29 g) was added to this solution at 0° C. and stirring was continued at room temperature for 4 hours. The reaction mixture was poured slowly into a large volume of iced water and the mixture was extracted with methylene chloride. The organic layer was washed successive with water, saturated aqueous sodium hydrogen carbonate, water, and then with saturated aqueous sodium chloride, dried, and then the solvent was evaporated. The residue was recrystallized from ethyl acetate/n-hexane to give colorless needles (20.14 g, yield: 74%). mp 77.5°–78.0° C.

Elemental Analysis $C_8H_4NOBr$ Calculated N: 5.74% C: 39.37% H: 2.48% Found N: 5.46% C: 39.53% H: 2.44%

NaH (1.61 g) was placed in a 500 ml three-neck flask and washed three times with n-hexane. Hexane was removed under reduced pressure, and after the substitution with argon gaseous atmosphere, DMF (50 ml) was added and NaH was suspended. Malonic acid diethylacetoamide (9.00 g) was dissolved in DMF (40 ml) and added to the reaction mixture at 0° C. After the gas generation ceased, the above-obtained nitro compound (9.93 g) was dissolved in DMF (50 ml) and added to the reaction mixture, and then stirring was continued at room temperature for 2.5 hours. After evaporation of DMF under reduced pressure, 2N HCl was added to the residue and the mixture was extracted with ethyl acetate. The organic layer was washed with water and saturated aqueous sodium chloride, dried over $MgSO_4$, and then the solvent was removed by evaporation. The residue was purified by chromatography using a silica gel column to give pale yellow powder (14.95 g, yield: 98%).

High Resolution MS: $C_{17}H_{20}N_2O_8$ Calculated 380.1219 Found 380.1217 n-Nonyltriphenylphosphonium bromide (4.47 g) was dissolved in THF (30 ml) and the solution was poured in a three-neck flask substituted with argon. The solution was cooled to 0° C. and then n-butyl lithium (9.5 mmol) was added to the solution. Stirring was continued at 0° C. for 90 minutes and then the solution was cooled to −78° C. A solution of the above product (2.18 g) in THF (10 ml) was mixed to the solution by dropwise addition. The reaction mixture was allowed to react at −78° C. for 90 minutes and then at 0° C. for 2 hours, and then the reaction was stopped by adding a small volume of 2N HCl. After THF was removed by evaporation under reduced pressure, 2N HCl was added to the residue and the mixture was extracted with ethyl acetate. The organic layer was washed successively with water and saturated aqueous sodium chloride, dried over $MgSO_4$, and then the solvent was removed by evaporation. The residue was purified using silica gel column chromatography (solvent: ethyl acetate/n-hexane=1:1) to give the desired product (1.07 g, yield: 56%).

The above olefin product (4.42 g) was dissolved in a mixture of acetic acid (20 ml) and concentrated hydrochloric acid (10 ml) and the mixture was gently refluxed for 7 hours. The solvent was removed by evaporation to give a tarry amino acid product. Ethanol (50 ml) was cooled over dry ice/acetone bath and maintained at a temperature below −20° C. and the thionyl chloride (12 g) was slowly added dropwise. The above amino acid was added to the reaction mixture and the mixture was stirred overnight at room temperature. After the solvent was removed by evaporation under reduced pressure, saturated aqueous sodium hydrogen carbonate was added to the residue and the mixture was extracted with ethyl acetate. The organic layer was washed successively with saturated aqueous sodium hydrogen carbonate, water, and then with saturated aqueous sodium chloride, dried over $MgSO_4$, and then the solvent was removed by evaporation. The residue was dissolved in methylene chloride (100 ml), and after the addition of excess $Boc_2O$, the solution was left overnight. The reaction mixture was concentrated under reduced pressure and purified using silica gel column chromatography (solvent: ethyl acetate/n-hexane=1:1).

The resulting compound was dissolved in THF (90 ml), and $LiBH_4$ (1.42 g) was added to the solution and stirring was continued at room temperature. The reaction solution was concentrated under reduced pressure, and the residue was carefully added to iced water and the mixture was extracted. The organic layer was washed successively with 10% aqueous citric acid, water, and then with saturated aqueous sodium chloride, dried over $MgSO_4$, and then the solvent was removed by evaporation. The residue was purified using silica gel column chromatography (solvent: ethyl acetate/n-hexane=1:1) to give colorless oil (2.32 g, yield: 59%).

The above-obtained hydroxyl compound (2.32 g) was dissolved in ethanol (20 ml), and 10% Pd/C (200 mg) was added to the solution and then stirring was continued for 7 hours under hydrogen gaseous atmosphere. The catalyst was removed by filtration and the resulting filtrate was concentrated. The residue was recrystallized from n-hexane to give colorless prisms (2.04 g, yield: 94%). mp 72°–73° C.

High Resolution MS: $C_{24}H_{42}N_2O_3$ Calculated 406.3195 Found 406.3179

A mixture of formic acid (1.21 g) and acetic anhydride (2.60 g) was heated at 60°–70° C. for 2 hours. The reaction mixture was cooled to 0° C., and then a solution of the above-obtained reduced product (2.04 g) in THF (30 ml) was added to the mixture and stirring was continued at room temperature for 6 hours. After evaporation of the solvent under reduced pressure, saturated aqueous sodium hydrogen carbonate was added to the residue and the mixture was extracted with ethyl acetate. The organic layer was washed successively with water and saturated aqueous sodium chloride, dried over $MgSO_4$, and then the solvent was removed by evaporation. The residue was purified using silica gel column chromatography (solvent: ethyl acetate/n-hexane=1:1) to give a formic acid ester as pale yellow oil (1.75 g, yield: 90%).

The above-obtained formic acid ester (1.61 g) was dissolved in THF (100 ml). A 1.0M solution of $BH_3$ in TMF (16 ml) was added to this solution and the mixture was stirred at 0° C. for 4 hours. After excess $BH_3$ was quenched by adding a small volume of 10% aqueous citric acid, the reaction mixture was concentrated under reduced pressure. A 10% aqueous solution of citric acid was added to the residue and the mixture was extracted with ethyl acetate. The organic layer was washed successively with water and saturated aqueous sodium chloride, dried over $MgSO_4$, and the solvent was removed by evaporation. The residue was purified using silica gel column chromatography (solvent: ethyl acetate/n-hexane=1:2) and recrystallized from ethyl acetate/ n-hexane to give colorless prisms (1.30 g, yield: 89%). mp 72°–73° C.

High resolution MS: $C_{25}H_{44}N_2O_3$ Calculated 420.3352 Found 420.3315

(±)-Benzyl 3-methyl-2-trifluoromethylsulfonyl-oxobutanoate was prepared from (DL)-Val according to the method of Kogan et al. (Kogan, T. P., Somers, T. C., Venuti, M. C., Tetrahedron, 1990, 6623). The above-obtained reduced compound (1.27 g) was dissolved in a mixture of dichloroethane (30 ml) and 2,6-lutidine (1.05 g), and then triflate (1.84 g) was added to the mixture and refluxed for 24 hours. The resulting reaction mixture was purified using silica gel column chromatography (methylene chloride/ethyl acetate=20:3) to give colorless oil (1.62 g, yield: 80%).

The above product (949 mg) was dissolved in methanol (120 ml). Pd/C (145 mg) was added to the solution and stirring was continued for 5 hours under hydrogen gaseous atmosphere. After the Pd/C was removed by filtration, the filtrate was concentrated. The resulting carboxylic acid and N-hydroxysuccinimide (400 mg) were dissolved in acetonitrile (20 ml). A DCC (336 mg) solution in acetonitrile (5 ml) was added to this solution and stirring was continued at room temperature. The solvent was evaporated under reduced pressure, and the residue was suspended in ethyl acetate. After insoluble materials were removed by filtration, the filtrate was concentrated.

Then the residue was subjected to silica gel column chromatography (solvent: ethyl acetate/methylene chloride= 1:5) to give colorless oil (917 mg, yield: 96%).

The above-obtained compound (1.28 g) was dissolved in $CH_3Cl$ (35 ml), and TFA (18 ml) was added to the solution at 0° C. and stirring was continued at room temperature for 2 hours. The solvent was removed by evaporation under reduced pressure and the residue was dissolved in 2 l of ethyl acetate. Saturated aqueous sodium hydrogen carbonate (120 ml) was added to the solution, and after a reflux for 6 hours, the reaction solution was cooled to room temperature and the aqueous layer was removed. The organic layer was washed with a small volume of saturated aqueous sodium chloride, dried over $MgSO_4$, and the solvent was removed by evaporation. The residue was purified using silica gel column chromatography (solvent: ethyl acetate) to give (±)-BL-V8-310 (394 mg, yield: 48%) and (±)-epi-BL-V8-310 (359 mg, yield: 45%).

(±)-BL-V8-310: colorless needles, mp 107°–108° C.

Elemental Analysis: $C_{25}H_{42}N_2O_2$ Calculated N: 6.96% C: 74.58% H: 10.51% Found N: 7.14% C: 74.57% H: 10.68%

(±)-epi-BL-V8-310: colorless flakes, mp 117°–118° C.

Elemental Analysis: $C_{25}H_{42}N_2O_2$ Calculated N: 6.96% C: 74.58% H: 10.51% Found N: 7.11% C: 74.33% H: 10.68%[{]jf44aExample 2

Preparation of (−)-BL-V8-310 and (−)-epi-BL-V8-310

(+)-Benzyl 3-methyl-2-trifluoromethylsulfonyl-oxobutanoate was prepared from (D)-Val according to the above-mentioned method of Kogan et al. From the reduced compound ($C_{25}H_{44}N_2O_3$, 154 mg), a benzyl compound was prepared in the same manner as in Example 1 (205 mg, yield: 90%), and then (−)-BL-V8-310 (55 mg, yield: 42%) and (−)-epi-BL-V8-310 (43 mg) were obtained.

(−)-BL-V8-310: colorless oil, $[\alpha]_D^{22}=-278.2°$ (c=0.64, $CHCl_3$)

(−)-epi-BL-V8-310: colorless oil, $[\alpha]_D^{22}=-140.3°$ (c=0.75, $CHCl_3$)

Example 3

Preparation of (+)-BL-V8-310 and (+)-epi-BL-V8-310

(−)-Benzyl 3-methyl-2-trifluoromethylsulfonyl-oxobutanoate was prepared from (L)-Val according to the above-mentioned method of Kogan et al. From the reduced compound ($C_{25}H_{44}N_2O_3$, 168 mg), a benzyl compound (184 mg) was prepared in the same manner as in Example 1 (yield:75%), and then (+)-BL-V8-310 (52 mg, yield:49%) and (+)-epi-BL-V8-310 (51 mg, yield:48%) were obtained.

(+)-BL-V8-310: colorless oil, $[\alpha]_D^{22}=+280.3°$ (c=0.61, $CHCl_3$)

(+)-epi-BL-V8-310: colorless oil, $[\alpha]_D^{22}=+137.1°$ (c=0.70,$CHCl_3$)

Example 4

Preparation of (±)-BL-V9-310 and (±)-epi-BL-V9-310

A nitro compound ($C_8H_4NOBr$, 10.19 g) prepared in the same manner as described in Example 1, 1,2-ethanediol (7.41 g), and p-toluenesulfonic acid (10 mg) were dissolved in toluene (100 ml) and the solution was refluxed for 3.5 hours while water was removed by azeotropic distillation using a Dean-Stark trap. The reaction mixture was cooled to room temperature, diluted with ethyl acetate, and then washed successively with saturated aqueous sodium hydrogen carbonate, water, and saturated aqueous sodium chloride. After the solution was dried over $MgSO_4$, the solvent was removed by evaporation. The residue was purified using silica gel column chromatography (solvent: methylene chloride) to give an acetal compound (11.64 g, yield: 97%).

The resulting acetal compound (6.90 g) was dissolved in toluene (60 ml), and after the addition of triphenylphosphine (6.90 g), the mixture was heated under reflux for 2 days. The precipitates formed were collected by filtration and washed with a small volume of toluene to give white powder (8.35 g, yield: 63%). mp 230°–235° C. (decomposition).

Elemental Analysis: $C_{28}H_{25}NO_4$ PBr Calculated N: 2.58% C: 61.10% H: 4.58% Found N: 2.40% C: 61.30% H: 4.57%

N-Boc-O-t-butylserine methyl ester (2.96 g) was dissolved in anhydrous toluene (140 ml) and the solution was cooled to –60° C. 1.5M diisobutylaluminum hydride (16 ml) was slowly added dropwise to the solution and stirring was continued at –60° C. for 1 hour. After the addition of a 10% aqueous citric acid (30 ml), the mixture was warmed up to room temperature and mixed with a 10% aqueous citric acid (100 ml). The aqueous layer was removed and the organic layer was washed with water and saturated aqueous sodium chloride, dried over $MgSO_4$, and then the solvent was removed by evaporation. The residue was purified using silica gel column chromatography (solvent: ethyl acetate/n-hexane=1:1) to give colorless oil (2.03 g, yield: 77%).

The above-obtained compound (7.49 g) was dissolved in DMF (50 ml), and potassium carbonate (1.80 g) was added to the solution and stirring was continued at room temperature for 1.5 hours. OHC—CH(NHBoc)CH$_2$OC(CH$_3$)$_3$ (2.99 g) dissolved in DMF (20 ml) was added to the solution and then the mixture was allowed to react at 95° C. for 7 hours. The solvent was removed by evaporation under reduced pressure and a 10% aqueous citric acid was added to the residue and then the mixture was extracted with ethyl acetate. The organic layer was washed with water and saturated aqueous sodium chloride, dried over $MgSO_4$, and then the solvent was removed by evaporation. The residue was purified using silica gel column chromatography (solvent: ethyl acetate/n-hexane=1:3) to give a cis-compound (1.91 g) and a trans-compound (3.00 g). Total yield was 92%.

Cis-compound: pale yellow needles, mp 71°–72 ° C.

Elemental Analysis: $C_{22}H_{32}N_2O_7$ Calculated N: 6.42% C: 60.54% H: 6.42% Found N: 6.33% C: 60.32% H: 6.33%

Trans-compound: pale yellow oil

High Resolution MS: $C_{22}H_{32}N_2O_7$ Calculated 436.2210 Found 436.2254

The above ketal compound (cis-compound, 2.85 g) and pyridinium p-toluenesulfonate (0.98 g) Were dissolved in acetone (40 ml) and water (3 ml) and then the mixture was refluxed for 15 hours. The reaction solution was concentrated under reduced pressure and the residue was washed successively with water and saturated aqueous sodium chloride, dried over $MgSO_4$, and then the solvent was removed by evaporation. The residue was purified using silica gel column chromatography (solvent: ethyl acetate/n-hexane=1:2) to give a benzaldehyde compound as pale yellow prisms (cis-compound, 2.03 g, yield: 79%). mp 103°–104° C.

Elemental Analysis: $C_{20}H_{28}N_2O_6$ Calculated N: 7.19% C: 61.21% H: 7.19% Found N: 7.07% C: 61.22% H: 7.29%

In a similar manner to those described above, benzaldehyde compound (trans-compound) was obtained from the ketal compound (trans-compound, 3.00 g) as pale yellow oil (1.78 g, yield: 66%).

High Resolution MS: $C_{20}H_{28}N_2O_6$ Calculated 392.1947 Found 392.1956

In a similar manner to those described in Example 1, the decenyl compound wherein —CH=CH—CH (NHBoc)— being a cis-configuration was obtained as pale yellow oil (758 mg, yield: 48%) from n-nonyltriphenylphosphonium bromide (1.97 g) and the above benzaldehyde compound (cis-compound, 589 mg). Similarly, using n-nonyltriphenylphosphonium bromide (2.95 g) and the above benzaldehyde compound (trans-compound, 1.78 g), the decenyl compound wherein —CH=CH—CH (NHBoc)— being a trans-configuration was obtained as pale yellow oil (1.10 g, yield: 48%).

In a similar manner to those described in Example 1, from the above nonenyl compound wherein —CH=CH—CH (NHBoc)— being a cis-configuration (758 mg), the reduced compound was obtained as colorless oil (613 mg, yield: 84%) in which two double bonds in the side chain were reduced.

High Resolution MS: $C_{30}H_{54}N_2O_3$ Calculated 490.4134 Found 490.4120

In a similar manner to those of Example 1, a benzyl compound was obtained as colorless oil (1.20 g, yield: 95%) by using the above reduced compound (913 mg). In addition, in a similar manner to those of Example 1, a succinylimide compound was prepared as pale yellow oil (1.11 g, yield: 78%) using the above benzyl compound (1.40 g), and successively in a similar manner to that of Example 1, (±)-BL-V9-310 (134 mg, yield: 20%) and (±)-epi-BL-V9-310 (112 mg, yield: 17%) were obtained using the above succinylimide compound (1.11 g).

(±)-BL-V9-310: colorless oil.

High Resolution MS: $C_{30}H_{52}N_2O_2$ Calculated 416.3402 Found 416.3442

(±)-epi-BL-V9-310: colorless needles, mp 146.5° C.

Elemental Analysis: $C_{30}H_{52}N_2O_2$ Calculated N: 6.72% C: 74.95% H: 10.64% Found N: 6.87% C: 75.02% H: 10.87%

Example 5

Preparation of (±)-BL-V8 and (±)-epi-BL-V8

DMF (100 ml) was added to NaH (5 g) washed with n-hexane, and then a solution of malonic acid diethylacetoamide (27 g) in DMF (50 ml) was added to the suspension. A solution of o-nitrobenzyl bromide (27 g) in DMF (50 ml) was further added to the above mixture at 0° C. and the mixture was left at room temperature overnight. The reaction mixture was poured into iced water, and the precipitates were collected by filtration and dissolved in methylene chloride. After dryness, the solvent was removed by evaporation and the residue was recrystallized from methylene chloride/hexane to give pale yellow needles (31.1 g, yield: 71%). mp 103°–104° C.

Elemental Analysis: $C_{16}H_{20}N_2O_7$ Calculated N: 7.95% C: 54.54% H: 5.72% Found N: 8.06% C: 54.66% H: 5.64%

The above compound (30.5 g) was refluxed for 70 minutes in an aqueous solution (150 ml) of NaOH (17.3 g, 5 equivalents) and then the mixture was cooled. The reaction mixture was acidified by adding concentrated sulfuric acid and the precipitates were collected by filtration. The precipitates were washed with a small volume of saturated aqueous sodium chloride and dried at 80° C. for 4 hours under reduced pressure. The resulting de-esterified compound was suspended in water (100 ml) and the suspension was refluxed for 3 hours. Then, the precipitates were collected by filtration, washed with saturated aqueous sodium chloride and dried over $P_2O_5$ at 80° C. for 6 hours under reduced pressure. $SOCl_2$ (23 ml) was slowly added to anhydrous ethanol (100 ml) at −10° C. and the mixture was left at −10° C. for 10 minutes. The above amino acid was added as solid to this solution. The reaction mixture was stirred at room temperature for 1 hour and at 60° C. for 3 hours, and then ethanol was removed by evaporation at 60° C. under reduced pressure. Sodium carbonate and water were added to the solution and the mixture was extracted with ethyl acetate. After evaporation of ethyl acetate, the resulting residue was dissolved in ethanol, and after the treatment of activated charcoal, the solvent was evaporated. The residue was purified using silica gel column chromatography (solvent: methylene chloride/ethyl acetate=8:1) to give an ester compound (14.8 g, yield: 61%). mp 72°–74° C.

Elemental Analysis: $C_{13}H_{16}N_2O_5$ Calculated N: 9.99% C: 55.71% H: 5.75% Found N: 9.99% C: 55.83% H: 5.70%

The above ester compound (14.5 g) was dissolved in ethanol saturated with hydrochloric acid (200 ml) and the solution was refluxed for 48 hours. After the addition of ether and cooling, the precipitates formed were collected by filtration, and washed sufficiently with ether to give an amino deprotected compound (hydrochloride) as colorless needles (12.3 g, yield: 86%). mp~204° C. (decomposition).

The above-obtained hydrochloride (12 g) was suspended in water (100 ml), and after the addition of excess amount of sodium hydrogen carbonate, the mixture was extracted with ethyl acetate. After dryness over $MgSO_4$, the solvent was removed by evaporation below 40° C. to give a free amino compound (9.8 g). The resulting product (9.06 g) was dissolved in a mixture of water (40 ml) and dioxane (40 ml), and after the addition of sodium hydrogen carbonate (8 g, 2.5 eq.), $Boc-N_3$ (10.9 g, 2 eq.) was added to the mixture. The mixture was stirred at 45°–50° C. for 40 hours using air cooling apparatus. Then, $Boc-N_3$(5.4 g, 1 eq.) and sodium hydrogen carbonate (4 g, 1 eq.) were further added and the reaction was continued for 24 hours. The reaction mixture was concentrated almost to dryness under reduced pressure, and water (200 ml) was added to the residue and the mixture was extracted with ethyl acetate. The organic layer was washed successively with a 0.5M aqueous sodium hydrogen carbonate, 0.5M aqueous citric acid, and then with water, dried over $MgSO_4$ and the solvent was removed by evaporation. The resulting residue was recrystallized from benzene to give a compound having an amino group protected by Boc group as pale yellow needles (10.73 g, yield: 83%). mp 97.5°–99° C.

Elemental Analysis: $C_{16}H_{22}N_2O_6$ Calculated N: 8.28% C: 56.80% H: 6.55% Found N: 8.40% C: 56.60% H: 6.56%

The above Boc compound (10.5 g) was dissolved in THF (150 ml), and $LiBH_4$ (1.5 g) was added to the solution at 0° C. and stirring was continued at 0° C. for 1 hour and additionally at room temperature for 3 hours. After then, water (200 ml) was carefully added to the solution and the mixture extracted with ethyl acetate. The organic layer was washed with water, dried over $MgSO_4$, and the solvent was evaporated to give hydroxymethyl compound (8.73 g, yield: 96%). mp 105°–106.5° C.

Elemental Analysis: $C_{14}H_{20}N_2O_5$ Calculated N: 9.45% C: 56.75% H: 6.80% Found N: 9.24% C: 56.72% H: 6.80%

The above-obtained compound (4.5 g) was dissolved in ethyl acetate/1% $H_2O$ (400 ml) and 10% Pd/C (2.5 g) was added to the solution. Hydrogen gas was introduced at 1 atm and the mixture was subjected to catalytic hydrogenation at room temperature for 2 hours. The Pd/C was removed by filtration and the filtrate was concentrated. The residue was recrystallized from benzene to give an aniline compound as colorless foliates (3.9 g, yield: 96%). mp 130.5°–131.5° C.

Elemental Analysis: $C_{14}H_{22}N_2O_3$ Calculated N: 10.52% C: 63.14% H: 8.33% Found N: 10.34% C: 63.44% H: 8.17%

The above compound (3.6 g) was dissolved in benzene (80 ml), and methyl 2-oxoisovalerate (4.4 g, 2.5 eq. ) was added to the solution. The mixture was allowed to reflux under the condition of azeotropic distillation under argon atmosphere for 24 hours. Methyl 2-oxoisovalerate (1.76 g) was added to the mixture and reflux was continued for 18 hours. Benzene and methyl 2-oxoisovalerate were evaporated under reduced pressure and the residue was dissolved in THF (120 ml). $NaBH_3CN$ (1.7 g, 2 eq.) was added to the solution and the mixture was left overnight at room temperature. The reaction mixture was concentrated to 20 ml at room temperature under reduced pressure, and after the addition of water, the mixture was acidified with citric acid and stirred for 2 hours. The solution was extracted with methylene chloride and the solvent was evaporated. The residue was purified using silica gel column chromatography (solvent: ethyl acetate/hexane=1:3). A mixture of the obtained imino compound and enamine compound was dissolved in methanol (300 ml). 10% Pd/C (4 g) was added to the solution and then hydrogen gas was introduced at 1 atm to carry out catalytic reduction at room temperature for 5 hours. An approximately sole reduction product was obtained, which was purified using silica gel column chromatography (solvent: ethyl acetate/hexane=1:4) to give colorless liquid (4.13 g, yield: 80%).

The above reduction product (4.05 g) was dissolved in methanol (50 ml), and after the addition of 2N potassium hydroxide (25 ml, 5 eq.), the mixture was left at room temperature for 24 hours. After the starting material disappeared on TLC plate, methanol was removed by evaporation at 40° C. This solution was acidified by adding a 10% aqueous citric acid and extracted with ethyl acetate to give a de-esterified compound. This product was immediately dissolved in $CH_3CN$ (30 ml), and after the addition of N-hydroxysuccinimide (2.45g, 2 eq.), and the solution was cooled below 0° C. A solution of DCC (3.29 g, 1.5 eq.) in $CH_3CN$ (10 ml) was added to the solution, and the mixture was left at 0° C. for 1 hours and then at room temperature for 2 hours. After evaporation of $CH_3CN$, the residue was dissolved in ethyl acetate and insoluble dicyclohexylurea was removed by filtration. The filtrate was concentrated and the residue was purified using silica gel column chromatography (solvent: ethyl acetate/hexane=1:1) to give colorless liquid (4.09 g, yield: 81%).

The above-obtained compound (4.05 g) was dissolved in methylene chloride (30 ml), and $CF_3COOH$ (30 ml) was added to the solution cooled to 0° C. The reaction mixture was left for 1 hours after substitution with argon atmosphere. $CF_3COOH$ was removed by evaporation at room temperature under reduced pressure, and after the addition of water (80 ml), an excess amount (approximately saturation) of sodium hydrogen carbonate was added to the mixture. After the addition of ethyl acetate (80 ml), the two-phase mixture was stirred and refluxed for 1 hours. The ethyl acetate layer was separated, and the aqueous layer was extracted twice with ethyl acetate. The organic layers were combined and the solvent was removed by evaporation. The residue was purified using silica gel column chromatography (solvent: ethyl acetate/methylene chloride=4:1) to give two different cyclized benzolactam isomers (total yield: 61%).

Isomer A: 644 mg, colorless prisms, mp 191°–193° C.

Elemental Analysis: $C_{14}H_{20}N_2O_2$ Calculated N: 11.28% C: 67.72% H: 8.12% Found N: 11.22% C: 67.81% H: 8.15%

Isomer B (epi-compound): 676 mg, colorless prisms, mp 187.5°–188.5° C.

Elemental Analysis: $C_{14}H_{20}N_2O_2$ Calculated N: 11.28% C: 67.72% H: 8.12% Found N: 11.22% C: 67.81% H: 8.15%

Each of the above isomers (300 mg) was dissolved in methanol (10 ml), and sodium hydrogen carbonate (500 mg) was added to the solution. After the addition of $CH_3I$ (12 ml), the mixture was refluxed for 85 hours. After evaporation of methanol and $CH_3I$, the residue was extracted with water and chloroform. The organic layer was concentrated and the resulting residue was purified using silica gel column chromatography (solvent: ethyl acetate/n-hexane= 3:1).

(±)-BL-V8: 206 mg (yield: 65%), colorless prisms, mp 133°–134° C.

Elemental Analysis: $c_{15}H_{22}N_2O_2$ Calculated N: 10.68% C: 68.67% H: 8.45% Found N: 10.72% C: 68.61% H: 8.57%

(±)-epi-BL-V8: 174 mg (yield: 55%), colorless needles, mp 155°–157° C.

Elemental Analysis: $C_{15}H_{22}N_2O_2$ Calculated N: 10.68% C: 68.67% H: 8.45% Found N: 10.62% C: 68.68% H: 8.69%

Example 6

Preparation of (±)-BL-V9 and (±)-epi-BL-V9

Methyl o-nitrophenyl acetate (11.3 g) was dissolved in THF (30 ml). A suspension of $LiBH_4$ (3.0 g) in THF (20 ml) was added to the solution under ice cooling. After stirring at 0° C. for 40 minutes and at room temperature for 3 hours, the solvent was removed by evaporation and concentrate the solution. The residue was poured into iced water and the mixture was extracted with methylene chloride. The organic layer was washed successively with a 10% aqueous citric acid, water, and with saturated aqueous sodium chloride, dried over $MgSO_4$, and the solvent was removed by evaporation to give yellow oil (8.09 g, yield: 84%).

The above compound (8.09 g) was dissolved in methylene chloride (10 ml) and the solution was cooled to −40° C. $PBr_3$ (5.8 g) was slowly added to this solution and stirring was continued at room temperature for 1 hour. This reaction mixture was poured into iced water (600 ml) and the mixture was extracted with methylene chloride. The organic layer was washed successively with water, saturated aqueous sodium hydrogen carbonate, water, and then with saturated aqueous sodium chloride, dried over $MgSO_4$, and then the solvent was removed by evaporation. The residue was purified using silica gel column chromatography to give pale yellow oil (5.52 g, yield: 41%).

NaH (7.3 g) was washed with n-hexane and dried under reduced pressure. After substitution with argon atmosphere, DMF (150 ml) was added to the NaH and the mixture was stirred. After the graduate addition of a solution of diethylacetoamide malonate (40.1 g) in DMF (150 ml), the mixture was stirred at room temperature for 30 minutes. A solution of the above-obtained bromo compound (39.1 g) in DMF (50 ml) was added to the solution and then stirring was continued at room temperature for 20 hours. The solvent was removed by evaporation under reduced pressure, and 2N HCl was added to the residue and the mixture was extracted with methylene chloride. The organic layer was washed successively with water and saturated aqueous sodium chloride, dried over $MgSO_4$, and then the solvent was evaporated. The residue was purified using silica gel column chromatography and recrystallized from methylene chloride/n-hexane to give colorless needles (50.4 g, yield: 81%). mp 75°–76° C.

Elemental Analysis: $C_{17}H_{22}NO_7$ Calculated N: 7.57% C: 55.60% H: 6.06% Found N: 7.65% C: 55.73% H: 6.05%

The above-obtained compound (5.16 g) was dissolved in acetic acid (12 ml) and concentrated hydrochloric acid (10 ml) and the mixture was refluxed for 9 hours. The reaction mixture was poured into iced water (200 ml) and washed twice with methylene chloride (50 ml). The aqueous layer was concentrated under reduced pressure, after removal of water by azeotropic distillation using a small volume of ethanol, the residue was dried under reduced pressure. Anhydrous ethanol (15 ml) was cooled to −20° C., and then thionyl chloride (6 ml) was mixed to the ethanol by dropwise addition while the solution temperature was maintained below −20° C. The above amino acid was added to this solution and stirring was continued at room temperature for 6 hours. The solvent was removed by evaporation under reduced pressure and a saturated aqueous sodium hydrogen carbonate was added to the residue and the mixture was extracted with ethyl acetate. The organic layer was washed successively with water and saturated aqueous sodium chloride, dried over $MgSO_4$, and the solvent was removed by evaporation. The residue was dissolved in methylene chloride (50 ml), and after the addition of $Boc_2O$ (5.14 g), the mixture was stirred at room temperature for 36 hours. After evaporation of the solvent under reduced pressure, the residue was purified using silica gel column chromatography to give pale yellow oil (4.83 g, yield: 97%).

High Resolution MS: $C_{17}H_2N_2O_6$ Calculated 352.1634 Found 352.1624

$LiBH_4$ (1.0 g) was suspended in THF (30 ml) and cooled at 0° C., and then a solution of the above Boc product (4.83 g) in THF (20 ml) was added to the suspension. After stirring at 0° C. for 1 hour and then at room temperature for 48 hours, the solvent was removed by evaporation. The residue was poured into iced water and the mixture was extracted with ethyl acetate. The organic layer was washed successively with a 10% aqueous solution of citric acid, water, and then with saturated aqueous sodium chloride, dried over $MgSO_4$, and the solvent was removed by evaporation. The residue was recrystallized from ethyl acetate/n-hexane to give a hydroxymethyl compound as pale yellow needles (2.67 g, yield: 63%). mp 109° C.

Elemental Analysis: $C_{15}H_{22}N_2O_5$ Calculated N: 9.03% C: 58.05% H: 7.14% Found N: 8.97% C: 58.27% H: 7.11%

The above-obtained compound (2.9 g) was dissolved in ethanol (300 ml) and Pd/C (300 mg) was added to the solution. After stirring 3 hours under hydrogen gaseous atmosphere, Pd/C was removed by filtration and the filtrate was concentrated. The residue was recrystallized from benzene to give an aniline compound as colorless needles (2.57 g, yield: 98%). mp 79°–80° C.

High Resolution MS: $C_{15}H_{24}N_2O_3$ Calculated 280.1787 Found 280.1760

The above-obtained compound (2.57 g) and methyl 2-oxoisovalerate (2.49 g) was dissolved in benzene (30 ml). The solution was refluxed for 24 hours while water was removed by azeotropic distillation using a Dean-Stark trap. The solvent was removed by evaporation under reduced pressure and the residue was dissolved in THF (30 ml). $NaBH_3CH$ (1.22 g) was added to the solution and stirring was continued at room temperature for 14 hours. The solvent was evaporated under reduced pressure and the residue was poured into iced water, and then the mixture was extracted with methylene chloride. The organic layer was washed successively with water and saturated aqueous sodium chloride, dried over MgSO$_4$, and the solvent was evaporated to give oily product. This product was dissolved in ethanol (150 ml), and after the addition of Pd/C (230 mg), the mixture was stirred for 4 hours under hydrogen gaseous atmosphere. Pd/C was removed by filtration and the filtrate was concentrated. The resulting residue was purified using silica gel column chromatography to give a condensed compound (1.92 g, yield: 52%).

The above-obtained compound (1.72 g) was dissolved in methanol (25 ml), and after the addition of 2N KOH aqueous solution (10 ml), the mixture was stirred at room temperature for 10 hours. The solvent was removed by evaporation under reduced pressure, and 10% aqueous citric acid was added to the resulting residue and then the mixture was extracted with ethyl acetate. The organic layer was washed twice with a saturated aqueous sodium chloride (50 ml), dried over MgSO$_4$, and then the solvent was evaporated to give a carboxylic acid compound. N-hydroxysuccinimide (1.03 g) and the above carboxylic acid were dissolved in acetonitrile (15 ml) and cooled to 0° C. A solution of DCC (1.39 g) in acetonitrile (10 ml) was added to this solution, and the reaction mixture was stirred at 0° C. for 20 minutes and then at room temperature for 2 hours. The acetonitrile was removed by evaporation under reduced pressure, and then the residue was dissolved in ethyl acetate and insoluble dicyclohexylurea was removed by filtration. The filtrate was concentrated and the residue was purified using silica gel column chromatography to give a succinimide compound (1.61 g, yield: 77%).

The above-obtained compound (1.61 g) was dissolved in methylene chloride (30 ml) and trifluoroacetic acid (5 ml) was added to the solution. This solution was stirred at room temperature for 50 minutes and then the solvent was removed by evaporation under reduced pressure. The residue was diluted with ethyl acetate (1 l), and after the addition of saturated aqueous sodium hydrogen carbonate (300 ml), the mixture was refluxed for 68 hours. The reaction mixture was cooled to room temperature and the aqueous layer was removed. The organic layer was washed with a saturated aqueous sodium chloride, dried over MgSO$_4$, and then the solvent was evaporated. The residue was purified using silica gel column chromatography and preparative thin layer chromatography to give two cyclized products: Isomer A (108 mg, yield: 12%) and Isomer B (158 mg, yield: 18%).

Isomer A: colorless prisms, mp 147°–148° C.

Elemental Analysis: C$_{15}$H$_{22}$N$_2$O$_2$ Calculated N: 10.68% C: 68.67% H: 8.45% Found N: 10.98% C: 68.96% H: 8.50%

Isomer B (epi-compound): colorless needles, mp 130°–131° C.

Elemental Analysis: C$_{15}$H$_{22}$N$_2$O$_2$ Calculated N: 10.68% C: 68.67% H: 8.45% Found N: 10.87% C: 68.37% H: 8.43%

A mixture of the above Isomer A (84 mg), sodium hydrogen carbonate (50 mg), methanol (3 ml) and CH$_3$I (5 ml) was refluxed for 7 days. The solvent was removed by evaporation under reduced pressure and the residue was purified using silica gel column chromatography to give (±)-BL-V9 as colorless oil (65 mg, yield: 74%).

High Resolution MS: C$_{16}$H$_{24}$N$_2$O$_2$ Calculated 276.1838 Found 276.1825

In a similar manner to the preparation of (±)-BL-V9, (±)-epi-BL-V9 was obtained as colorless needles (69 mg, yield: 93%) from 70 mg of the above Isomer B (epi-compound). mp 164°–165° C.

Elemental Analysis: C$_{16}$H$_{24}$N$_2$O$_2$ Calculated N: 9.84% C: 69.27% H: 8.83% Found N: 10.14% C: 69.53% H: 8.75%

Example 7

Preparation of (±)-BL-V10 and (±)-epi-BL-V10

LiBH$_4$ (6.1 g) was dissolved in THF (350 ml), and then a solution of 2-nitorocinnamic acid methyl ester (27.3 g) in THF (100 ml) was added to the solution and stirring was continued at room temperature for 22 hours. The solvent was removed by evaporation under reduced pressure, and then ice water was added to the residue and the mixture was extracted with ethyl acetate. The organic layer was washed successively with water and saturated aqueous sodium chloride, dried over MgSO$_4$, and then the solvent was evaporated to give a colorless oily product in which a double bond and an ester group were reduced (15.2 g, yield: 63.5%). In a similar manner to that of the bromination process according to Example 6, a bromo compound was obtained as pale yellow oil (9.2 g, yield: 45%) from the above reduction product (15.2 g), and a malonic acid ester adduct was obtained as pale yellow oil (9.99 g, yield: 69%) from the bromo compound (9.23 g).

High Resolution MS: C$_{18}$H$_{24}$N$_2$O$_7$ Calculated 380.1584 Found 380.1546

In a similar manner to those described in Example 6, decarbonation and Boc-derivatization were carried and an amino ester compound whose amino group was protected by Boc was obtained as pale yellow oil (7.7 g, yield:80%) from the above malonic acid ester adduct (9.99 g).

High Resolution MS: C$_{18}$H$_{26}$N$_2$O$_6$ Calculated 366.1791 Found 366.1762

The above compound (4.71 g) was dissolved in ethanol (200 ml), and after the addition of Pd/C (620 mg), the mixture was stirred for 4 hours under hydrogen gas flow. Pd/C was removed by filtration and the filtrate was concentrated. The residue was dissolved in THF (10 ml) and the solution was added to a mixed acid anhydride prepared by heating acetic anhydride (5.52 g) and formic acid (3.16 g) at 50°–60° C. for 2 hours. The reaction mixture was stirred at room temperature for 4.5 hours and the solvent was removed by evaporation under reduced pressure. A saturated aqueous sodium hydrogen carbonate was added to the residue and then the mixture was extracted with ethyl acetate. The organic layer was washed successively with water and saturated aqueous sodium chloride, dried over MgSO$_4$, and then the solvent was evaporated. The residue was purified using silica gel column chromatography to give a formanilide compound as colorless oil (4.05 g, yield: 87%).

High Resolution MS: C$_{19}$H$_{28}$N$_2$O$_5$ Calculated 364.1998 Found 364.1955

The above compound (3.55 g) was dissolved in THF (100 ml) and cooled to 0° C. A 1.0M solution of BH$_3$ in THF (20 ml) was added to the solution and stirring was continued at 0° C. for 2 hours. A 10% aqueous citric acid (10 ml) was added to the reaction mixture and then the solvent was evaporated. Water was added to the residue and the mixture was extracted with ethyl acetate. The organic layer was washed successively with water and saturated aqueous sodium chloride, dried over MgSO$_4$, and then the solvent was evaporated. The residue was purified using silica gel column chromatography to give a methylaniline compound as colorless needles (3.00 g, yield: 88%).

Elemental Analysis: C$_{19}$H$_{30}$N$_2$O$_4$ Calculated N: 7.99% C: 65.12% H: 8.63% Found N: 7.99% C: 65.17% H: 8.65%

LiBH$_4$ (1.50 g) was dissolved in THF (150 ml) and cooled to 0° C. A solution of the above compound (6.84 g) in THF (50 ml) was added to the solution and stirring was continued at 0° C. for 1 hour and then at room temperature for 4 hours.

The solvent was removed by evaporation under reduced pressure and the residue was poured into iced water and the mixture was extracted with methylene chloride. The organic layer was washed successively with 10% aqueous solution of citric acid, water, and then with saturated aqueous sodium chloride, dried over $MgSO_4$, and then the solvent was evaporated. The residue was purified using silica gel column chromatography to give a hydroxymethyl compound as colorless needles (5.99 g). mp 100° C.

Elemental Analysis: $C_{17}H_{28}N_2O_3$ Calculated N: 9.08% C: 66.20% H: 9.15% Found N: 8.99% C: 66.34% H: 9.25%

(±)-Benzyl 3-methyl-2-trifluoromethylsulfonyl-oxobutanoate was prepared from (DL)-Val according to the method of Kogan et al. (Kogan, T. P., Somers, T. C., Venuti, M. C., Tetrahedron, 1990, 6623) and then reacted with the above-obtained compound (3.37 g) in a similar manner to those described in Example 1 to give pale yellow oil (2.91 g, yield: 53%). The product was further subjected to catalytic hydrogenation and succinimidation in a manner similar to those described in Example 1 to give colorless oil (2.05 g, yield: 77%) from the above-obtained compound (2.91 g).

The above-prepared compound (2.05 g) was dissolved in methylene chloride (10 ml), and after the addition of trifluoroacetic acid (15 ml), the mixture was stirred at 0° C. for 30 minutes and then at room temperature for 4 hours. The solvent was removed by evaporation under reduced pressure and the residue was diluted with ethyl acetate (1 l). After the addition of saturated aqueous sodium hydrogen carbonate (100 ml), the mixture was heated under reflux for 2 days. The reaction mixture was cooled to room temperature and the aqueous layer was removed. The organic layer was washed with saturated aqueous sodium chloride, dried over $MgSO_4$, and then the solvent was evaporated. The residue was purified using silica gel column chromatography to give a mixture of BL-V10 and epi-BL-V10 (436 mg). The two isomers were separated by acetylation according to the following procedures: The above mixture (436 mg) was dissolved in pyridine (10 ml) and acetic anhydride (2 ml) and then the mixture was stirred at room temperature for 2 hours. The solvent was removed by evaporation under reduced pressure and 2N HCl was added to the residue and then the mixture was extracted with ethyl acetate. The organic layer was washed successively with water and saturated aqueous sodium chloride, dried over $MgSO_4$, and then the solvent was evaporated. The residue was purified using silica gel column chromatography and preparative thin layer chromatography to give Isomer A (206 mg, yield:41%) and Isomer B (epi-compound, 205 mg, yield: 41%).

Isomer A: colorless prisms, mp 130.5°–°131.5° C.

Elemental Analysis: $C_{19}H_{28}N_2O_3$ Calculated N: 8.43% C: 68.65% H: 8.49% Found N: 8.33% C: 68.47% H: 8.57%

Isomer B (epi-compound): colorless plates, mp 102°–102.5° C.

Elemental Analysis: $C_{19}H_{28}N_2O_3$ Calculated N: 8.43% C: 68.65% H: 8.49% Found N: 8.62% C: 68.39% H: 8.70%

The above Isomer A (53 mg) was dissolved in methanol (6 ml), and after the addition of a few drops of 4N KOH, the mixture was stirred at room temperature for 100 minutes. The solvent was removed by evaporation under reduced pressure and 2N hydrochloric acid was added to the residue and the mixture was extracted with ethyl acetate. The organic layer was washed successively with water and saturated aqueous sodium chloride, dried over $MgSO_4$, and then the solvent was evaporated. The residue was purified using silica gel column chromatography and recrystallized from ethyl acetate/n-hexane to give (±)-BL-V10 as colorless plates (38 mg, yield: 83%). mp 124°–126° C.

Elemental Analysis: $C_{17}H_{26}N_2O_2$ Calculated N: 9.65% C: 70.31% H: 9.02% Found N: 9.54% C: 70.20% H: 9.01%

In a similar manner to the preparation of(±)-BL-V10, (±)-epi-BL-V10 was obtained as colorless needles (21 mg, yield: 83%) from the above Isomer B (32 mg). mp 157°–158° C.

Elemental Analysis: $C_{17}H_{26}N_2O_2$ Calculated N: 9.65% C: 70.31% H: 9.02% Found N: 9.61% C: 70.22% H: 9.31%

Example 8

Preparation of (−)-BL-V8-210 and (−)-epi-BL-V8-210

2-Nitro-5-methylbenzoic acid (20.2 g) was dissolved in thionyl chloride (17.0 g) and anhydrous benzene (50 ml) and the solution was heated under reflux. The solvent was removed by evaporation under reduced pressure, and then anhydrous methanol was added to the residue and stirring was continued for 8 hours. The solvent was removed by evaporation under reduced pressure and then 2N HCl was added to the residue and the mixture wad extracted with ethyl acetate. The organic layer was washed successively with water, saturated aqueous sodium hydrogen carbonate, water, and then with saturated aqueous sodium chloride, dried over $MgSO_4$, and then the solvent was evaporated. The residue was recrystallized from ethyl acetate to give a methyl ester compound as colorless plates (17.9 g, yield: 82%). mp 75°–77° C.

Elemental Analysis: $C_9H_9NO_4$ Calculated N: 7.18% C: 55.39% H: 4.65% Found N: 7.41% C: 55.20% H: 4.43%

The above-obtained ester compound (20.1 g) was dissolved in a mixture of acetic acid (120 ml) and acetic anhydride (120 ml) and cooled to −20° C. While the temperature was kept at −20° C., concentrated sulfuric acid (40 ml) was added dropwise to the solution and then anhydrous chromic acid (30.4 g) was added in about 2 g portions. The reaction mixture was stirred at 0° C. for 2 hours and at room temperature for 14 hours, and then poured into iced water. This mixture was extracted with ethyl acetate and the organic layer was washed successively with water and saturated aqueous sodium chloride, dried over $MgSO_4$, and then the solvent was evaporated. The residue was recrystallized from ethyl acetate/n-hexane to give colorless plates (18.2 g, yield: 78%). mp 196°–199° C.

Elemental Analysis: $C_9H_7NO_6$ Calculated N: 6.22% C: 48.01% H: 3.13% Found N: 6.24% C: 47.89% H: 2.96%

The above-obtained compound (22.6 g) was dissolved in THF (450 ml) and cooled to 0° C., and after the addition of 10.0M $BH_3SMe$ (16.0 ml), the mixture was stirred at room temperature for 30 minutes and heated under reflux for 5 hours. After a small volume of methanol was added to the reaction solution, the mixture was refluxed for 10 minutes and then the solvent was evaporated. A saturated aqueous sodium hydrogen carbonate was added to the residue and the mixture was extracted with ethyl acetate. The organic layer was washed successively with water and saturated aqueous sodium chloride, dried over $MgSO_4$, and then the solvent was evaporated. The resulting residue was recrystallized from ethyl acetate/n-hexane to give a benzyl alcohol compound as colorless needles (19.2 g, yield: 91%). mp 52.5°–53° C.

Elemental Analysis: $C_9H_9NO_5$ Calculated N: 6.63% C: 51.19% H: 4.30% Found N: 6.68% C: 51.34% H: 4.19%

The above-obtained compound (15.5 g) was dissolved in anhydrous methylene chloride (250 ml), and after the addition of pyridinium chlorochromate (16.8 g) and alumina (21.1 g), the mixture was stirred for 18 hours. The reaction mixture was subjected to ordinary post-treatments and then the resulting crude product was purified using silica gel column chromatography to give a benzaldehyde compound as pale yellow plates (14.4 g, yield: 94%). mp 74.5°–75° C.

Elemental Analysis: $C_9H_7NO_5$ Calculated N: 6.70% C: 51.68% H: 3.37% Found N: 6.74% C: 51.66% H: 3.25% n-Nonyltriphenylphosphonium bromide (45.8 g) was dissolved in THF (800 ml) and cooled to 0° C., and after the dropwise addition and mixing of 1.6M n-BuLi (30 ml), the mixture was stirred at 0° C. for 40 minutes. The above compound (8.83 g) was added to the solution and stirring was continued at 0° C. for 30 minutes and then at room temperature for 3.5 hours. After the addition of a small amount of 2N HCl, the solvent was removed by evaporation under reduced pressure. 2N HCl was added to the residue and the mixture was extracted with methylene chloride. The organic layer was washed successively with water and saturated aqueous sodium chloride, dried over $MgSO_4$, and then the solvent was evaporated. The residue was purified using silica gel column chromatography (solvent: methylene chloride/n-hexane=1:1) to give a decenyl compound as pale yellow oil (11.3 g, yield: 84%).

$LiBH_4$ (2.7 g) was dissolved in THF (500 ml), and after the addition of the above compound (11.2 g), the mixture was stirred at room temperature for 16 hours. The solvent was removed by evaporation under reduced pressure, and then water was added to the residue and the mixture was extracted with ethyl acetate. The organic layer was washed successively with water, 10% aqueous citric acid, water, and then with saturated aqueous sodium chloride, dried over $MgSO_4$, and then the solvent was evaporated. The residue was purified using silica gel column chromatography (solvent: methylene chloride/ethyl acetate=10:1) to give a hydroxymethyl compound of which methyl ester was reduced as pale yellow oil (7.64 g, yield: 82%).

NaH 1.20 g was washed with n-hexane and dried under reduced pressure. After substitution with argon atmosphere, toluene (40 ml) was added to prepare a suspension. A solution of the above-obtained compound (0.64 g) in toluene (80 ml) was added to the suspension. A solution of p-toluenesulfonyl chloride (5.75 g) in toluene (50 ml) was further added to the mixture and then stirring was continued at 0° C. for 2 hours. The reaction mixture was poured into a 10% aqueous citric acid and the mixture was extracted with ethyl acetate. The organic layer was washed successively with water and saturated aqueous sodium chloride, dried over $MgSO_4$, and then the solvent was evaporated. The residue was purified using silica gel column chromatography (solvent: methylene chloride/n-hexane=1:1) as pale red oil (10.77 g, yield: 92%) to give a compound in which the hydroxyl group was tosylated.

NaH (1.15 g) was washed with n-hexane and dried under reduced pressure. After substitution with argon atmosphere, the NaH was suspended in DMF (150 ml), and after the addition of diethyl acetoaminomalonate (6.67 g), the mixture was stirred at room temperature for 30 minutes. A solution of the above-obtained tosyl compound (10.77 g) in DMF (100 ml) was added to the reaction mixture and stirring was continued at room temperature for 15.5 hours. A small volume of 2N HCl was added to the reaction mixture, and then the solvent was removed by evaporation under reduced pressure. 2N HCl was added to the residue and the mixture was extracted with ethyl acetate. The organic layer was washed successively with water and saturated aqueous sodium chloride and then dried over $MgSO_4$. After the solvent was removed by evaporation under reduced pressure, the residue was purified using silica gel column chromatography (solvent: methylene chloride/ethyl acetate= 10:1) to give a malonic acid ester adduct as pale yellow prisms (9.12 g, yield: 77%).

Elemental Analysis: $C_{26}H_{38}N_2O_7$ Calculated N: 5.71% C: 63.65% H: 7.81% Found N: 5.74% C: 63.44% H: 7.90%

The above-obtained compound (9.12 g) was dissolved in a mixture of acetic acid (20 ml) and concentrated hydrochloric acid (50 ml). After reflux for 24 hours, the solvent was removed by evaporation under reduced pressure to give an amino acid compound. Anhydrous ethanol (100 ml) was cooled to −40° C., and thionyl chloride (20.86 g) was added dropwise and mixed to the ethanol while the temperature was kept below −20° C. A solution of the above-obtained amino acid in anhydrous ethanol (40 ml) was added to the mixture at −40° C. The reaction mixture was stirred at −40° C. for 1 hour and then at room temperature for 30 hours. The solvent was evaporated under reduced pressure and a saturated aqueous sodium hydrogen carbonate was added to the residue and the mixture was extracted with ethyl acetate. The organic layer was washed successively with water and saturated aqueous sodium chloride, dried over $MgSO_4$, and then the solvent was evaporated. The resulting residue was dissolved in methylene chloride (200 ml), and after the addition of $Boc_2O$ (5.04 g), the mixture was stirred at room temperature for 18 hours. The solvent was removed by evaporation under reduced pressure and the residue was purified using silica gel column chromatography (solvent: methylene chloride) to give an ethyl ester compound as pale yellow oil (8.10 g, yield: 91%) having an amino group protected with Boc group.

$LiBH_4$ (1.28 g) was suspended in THF (150 ml) and cooled to 0° C. A solution of the above compound (8.10 g) in THF (50 ml) was added to the suspension and stirring was continued at 0° C. for 1 hour and then at room temperature for 17.5 hours. The solvent was removed by evaporation under reduced pressure, and then water was added to the residue and the mixture was extracted with methylene chloride. The organic layer was washed successively with water and saturated aqueous sodium chloride, dried over $MgSO_4$, and then the solvent was evaporated. The residue was purified using silica gel column chromatography to give a hydroxymethyl compound as colorless needles (3.93 g, yield: 49%). mp 91°–93° C.

Elemental Analysis: $C_{24}H_{38}N_2O_5$ Calculated N: 6.45% C: 66.33% H: 8.81% Found N: 6.49% C: 66.20% H: 8.76%

The above compound (2.44 g) was dissolved in methanol (200 ml). Pd/C (240 mg) was added to the solution and stirring was continued for 10 hours under hydrogen gaseous atmosphere. After removal of Pd/C by filtration, the filtrate was concentrated. The residue was recrystallized from ethyl acetate/n-hexane to give a reduction product as colorless prisms (2.09 g, yield: 92%) in which a double bond in the side chain and a nitro group were reduced. mp 115° C.

Elemental Analysis: $C_{24}H_{42}N_2O_3$ Calculated N: 6.89% C: 70.89% H: 10.41% Found N: 6.82% C: 70.69% H: 10.19%

A mixture of formic acid (1.22 g) and acetic anhydride (2.66 g) was stirred at 75°–80° C. for 3 hours, and after the addition of THF (5 ml), the mixture was cooled to 0° C. A solution of the above reduced compound (1.99 g) in THF (30 ml) was added to the mixed acid anhydride and stirring was continued at 0° C. for 30 minutes and then at room temperature for 2 hours. The solvent was removed by evaporation under reduced pressure, and then a saturated aqueous sodium hydrogen carbonate was added to the residue and the mixture was extracted with ethyl acetate. The organic layer was washed successively with water and saturated aqueous sodium chloride, dried over MgSO$_4$, and then the solvent was evaporated. The residue was purified using silica gel column chromatography (solvent: ethyl acetate/n-hexane= 1:1) to give a formanilide compound as colorless needles (1.97 g, yield:93%). mp 93° C.

Elemental Analysis: C$_{25}$H$_{42}$N$_2$O$_4$ Calculated N: 6.45% C: 69.09% H: 9.74% Found N: 6.47% C: 68.81% H: 9.57%

The above-obtained compound (1.89 g) was dissolved in THF (300 ml) and cooled to 0° C., and after the addition of 1.0M solution of BH$_3$ in THF (19.0 ml), the mixture was stirred at 0° C. for 2.5 hours. A 10% aqueous solution of citric acid was added to the reaction mixture and then the solvent was removed by evaporation under reduced pressure. A saturated aqueous sodium hydrogen carbonate was added to the residue and then the mixture was extracted with ethyl acetate. The organic layer was washed successively with water, saturated aqueous sodium chloride, dried over MgSO$_4$, and then the solvent was evaporated. The residue was purified using silica gel column chromatography (solvent: ethyl acetate/n-hexane=1:1) to give methylaniline compound as colorless prisms (1.82 g, yield: 99%). mp 53°–55° C.

Elemental Analysis: C$_{25}$H$_{44}$N$_2$O$_3$ Calculated N: 6.66% C: 71.39% H: 10.54% Found N: 6.67% C: 71.12% H: 10.45%

In a similar manner to those described in Example 1, (+)-benzyl 3-methyl-2-trifluoromethylsulfonyl-oxobutanoate (808 mg) was reacted with the above-obtained compound (878 mg) to give colorless oil (1.095 g, yield: 86%). Catalytic hydrogenation and succinimidation were carried out in similar manners to those of Example 1 to give colorless oil (930 mg, yield: 84%) from 1.09 g of the above compound.

In a similar manner to those of Example 1, (–)-BL-V8-210 (240 mg, yield: 40%) and (–)-epi-BL-V8-210 (231 mg, yield: 38%) were obtained from the above compound (930 mg).

(–)-BL-V8-210: colorless oil, $[\alpha]_D^{22}=-231.9°$ (c=1.16, CHCl$_3$)

(–)-epi-BL-V8-210: colorless oil, $[\alpha]_D^{22}=-145.9°$ (c=0.92,CHCl$_3$)

(–)-Benzyl 3-methyl-2-trifluoromethylsulfonyl-oxobutanoate (515 mg) was reacted with the above methylaniline compound (701 mg) in a similar manner to those described in Example 1, colorless oil was obtained (849 mg, yield:83%). In similar manners to those of Example 1, catalytic hydrogenation and succinimidation were carried out to give colorless oil (688 mg, yield: 80%) from the above compound (849 mg).

In a similar manner to that of Example 1, (+)-BL-V8-210 (209 mg, yield: 47%) and (+)-epi-BL-V8-210 (193 mg, yield: 43%) were obtained from the above compound (688 mg).

(+)-BL-V8-210: colorless oil, $[\alpha]_D^{22}=+239.8°$ (c=0.95, CHCl$_3$)

(+)-epi-BL-V8-210: colorless oil, $[\alpha]_D^{22}=+147.4°$ (c=1.00,CHCl$_3$)

Example 9

Preparation of (–)-BL-V8-N10 and (+)-epi-BL-V8-N10 and (+)-epi-BL-V8-N10

The aniline compound prepared in Example 5 (C$_4$H$_{22}$N$_2$O$_3$, mp 130.5°–131.5° C., 1.37 g) was dissolve in anhydrous methanol (35 ml). n-Caprinaldehyde (1.22 g) and NaBH$_3$CN (0.55 g) were added to the solution, and stirring was continued at room temperature for 3 days.

The solvent was removed by evaporation under reduced pressure, and 10% aqueous citric acid was added to the residue and the mixture was extracted with ethyl acetate. The organic layer was washed successively with water and saturated aqueous sodium chloride, dried over MgSO$_4$, and then the solvent was evaporated. The residue was purified using silica gel column chromatography (solvent: ethyl acetate/n-hexane=1:2) to give N-decanyl compound as colorless needles (977 mg, yield: 47%). mp 52°–54° C.

The above compound (590 mg) was dissolved in 2,6-lutidine (3.0 ml), and after the addition of (+)-benzyl 3-methyl-2-trifluoromethylsulfonyl-oxobutanote (550 mg), the mixture was stirred at 110° C. for 5 days. After the reaction mixture was subjected to post-treatments, the crude product was purified using silica gel column chromatography to give colorless oil (80 mg, yield: 10%). In a similar manner to that of Example 1, (–)-epi-BL-V8-N10 (53 mg, yield: 49%) was obtained as colorless oil from the above-obtained compound (160 mg): $[\alpha]_D^{22}=-114.5°$ (c=1.21, CHCl$_3$)

Similarly, colorless oil was obtained (75 mg, yield: 9%) from (–)-benzyl 3-methyl-2-trifluoromethylsulfonyl-oxobutanoate (260 mg) and the above N-decanyl compound (605 mg). In a similar manner to that of Example 1, (+)-epi-BL-V8-N10 was obtained as colorless oil (36 mg, yield: 41%) from the above-obtained compound (132 mg): $[\alpha]_D^{22}=+112.6°$ (c=0.95,CHCl$_3$)

Example 10

Preparation of (–)-BL-V8-C10 and (–)-epi-BL-V8-C10

By using the aniline compound prepared in Example 5 (C$_{14}$H$_{22}$N$_2$O$_3$, mp 130.5°–131.5° C., 1.50 g), a formanilide compound (1.26 g, yield: 76%) was obtained as pale yellow oil in a similar manner to the preparation of the formanilide compound according to Example 8. The product was further reduced with BH$_3$ according to the method of Example 8 and a methylaniline compound was obtained as colorless prisms (950 mg, yield: 79%) from the above-obtained compound (1.26 g). mp 102°–104° C.

Elemental Analysis: C$_{15}$H$_{24}$N$_2$O$_3$ Calculated N: 9.99% C: 64.26% H: 8.63% Found N: 9.75% C: 64.22% H: 8.71%

Metallic sodium (6.70 g) was dissolved in anhydrous ethanol (350 ml) and diethyl acetoaminomalonate (66.0 g) was added to the solution. The solution was stirred at room temperature for 30 minutes, and after the addition of n-decyl bromide (68.95 g), the mixture was stirred at room temperature for 1 hour and then heated under reflux for 1 hour. The solvent was removed by evaporation under reduced pressure, and then 2N hydrochloric acid was added to the residue and the mixture was extracted with methylene chloride. The organic layer was washed successively with water and saturated aqueous sodium chloride, dried over MgSO$_4$, and then the solvent was evaporated. The residue was purified using silica gel column chromatography to give a malonic acid ester adduct as colorless irregular crystals (99.1 g, yield: 95%). mp 45°–46° C.

Elemental Analysis: C$_{19}$H$_{35}$NO$_5$ Calculated N: 3.92% C: 63.84% H: 9.87% Found N: 4.10% C: 64.07% H: 9.97%

The above obtained compound (99.1 g) was dissolved in acetic acid (120 ml) and concentrated hydrochloric acid (100 ml), and then the mixture was heated under reflux for 6.5 hours. Water (1 l) was added to the reaction mixture and the mixture was neutralized with a 4N aqueous sodium hydroxide. After the solution was sufficiently cooled, the precipitates were collected by filtration. The resulting precipitates were washed with a small volume of water, methanol and then with ether, and dried under reduced pressure to give (±)-n-decanylglycine as colorless powder (53.8 g, yield: 90%). mp 220° C. (decomposition).

The above compound (51.1 g) was dissolved in a 2N aqueous sodium hydroxide (120 ml) and cooled to 0° C. Chloroacetyl chloride (62 g) was dissolved in a 2N aqueous sodium hydroxide (200 ml) and added dropwise and mixed to the above solution at 0° C. over 2 hours.

The pH of the reaction mixture was adjusted to 1 to 2 by adding concentrated hydrochloric acid and then the precipitates were collected by filtration. The resulting precipitates were dissolved in ethyl acetate, washed successively with water and saturated aqueous sodium chloride, dried over $Na_2SO_4$, and then the solvent was removed by evaporation. The residue was recrystallized from acetone/n-hexane to give an acylamino compound as colorless needles (20.5 g, yield:63%). mp 91° C.

Elemental Analysis: $C_{14}H_{26}NO_3Cl$ Calculated N: 4.84% C: 57.62% H: 8.98% Found N: 4.68% C: 57.91% H: 8.79%

The above acylamino compound (22.56 g) and sodium hydroxide (3.44 g) were dissolved in purified water (800 ml). The solution was adjusted to pH 7.27 by adding 3N hydrochloric acid and further diluted with purified water (2 l). Aspergillus amino acylase (Tokyo Kasei Co., Ltd., Japan, 3.58 g) and cobalt chloride (15 mg) were added to the above solution and the mixture was left stand at 37° C. for 19 hours. The precipitates were collected from the reaction mixture by filtration and dried under reduced pressure to give (S)-n-decanylglycine as colorless powder (8.22 g, yield: 49%). mp 220° C.

The above filtrate was left stand at 37° C. for additional 22 hours and then filtered. The filtrate was adjusted to pH 1 with concentrated hydrochloric acid and precipitates formed were collected by filtration. The precipitates were dissolved in ethyl acetate, washed successively with a 2N hydrochloric acid, water, and then with saturated aqueous sodium chloride, dried over $MgSO_4$, and then the solvent was removed by evaporation. The residue was recrystallized from acetone/n-hexane to give an aminoacyl compounds of (R)-n-decanylglycine as colorless plates (7.92 g, yield: 35%) mp 79°–80.5° C.

Elemental Analysis: $C_{14}H_{26}NO_3Cl$ Calculated N: 4.84% C: 57.62% H: 8.98% Found N: 4.79% C: 57.84% H: 9.15%

The above-obtained (R)-aminoacyl compound (5.60 g) was suspended in 3N hydrochloric acid (100 ml) and the suspension was refluxed for 4.5 hours. The reaction mixture was neutralized with aqueous ammonia and the precipitates were collected by filtration. The resulting precipitates was washed with a small volume of water, methanol, and then with ethyl acetate, and dried under reduced pressure to give (R)-n-decanylglycine as colorless powder (4.74 g, yield: 99%). mp 205° C. (decomposition).

(R)-n-Decanylglycine (2.69 g) was dissolved in 2N sulfuric acid (100 ml) and heated to 95° C. An aqueous solution (23 ml) of sodium nitrite (2.00 g) was added dropwise to the reaction mixture over 1 hour and stirring was continued at 95° C. for 2.5 hours. The reaction mixture was extracted with ethyl acetate and the organic layer was washed with saturated aqueous sodium chloride, dried over $MgSO_4$, and then the solvent was evaporated. The residue was dissolved in anhydrous benzene (50 ml) and benzyl alcohol (8.5 ml), and after the addition of thionyl chloride (1.0 ml), the mixture was refluxed for 10 hours while water was removed by azeotropic distillation using a Dean-Stark trap. Thionyl chloride (1.0 ml) was added to the reaction mixture and the mixture was further refluxed for 16 hours. The solvent was removed by evaporation under reduced pressure, a saturated aqueous sodium hydrogen carbonate was added to the residue and the mixture was extracted with ethyl acetate. The organic layer was washed successively with water, 10% aqueous citric acid, water, and then with saturated aqueous sodium chloride, dried over $MgSO_4$, and then the solvent was evaporated. The residue was purified using silica gel column chromatography to give a (R)-hydroxybenzyl ester compound as colorless oil (2.04 g, yield: 53%): $[\alpha]_D^{22}$=+10.46° (c=1.09,$CHCl_3$).

The above compound (1.17 g) was dissolved in anhydrous methylene chloride (20 ml) and 2,6-lutidine (0.95 g) and cooled to –40° C. After the addition of anhydrous triflate (1.92 g), the mixture was stirred at –40° C. for 1 hour. Water was added to the reaction mixture and the mixture was extracted with methylene chloride. The organic layer was washed with water and saturated aqueous sodium chloride, dried over $MgSO_4$, and then the solvent was evaporated. The residue was purified using silica gel column chromatography (solvent: ethyl acetate/n-hexane=1:5) to give (R)-triflate compound as colorless liquid (1.24 g, yield: 74%):

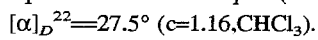

According to the method of Example 1, colorless oil (1.01 g, yield: 80%) was obtained from the above-obtained methylaniline compound (mp 102°–104° C., $C_{15}H_{24}N_2O_3$, 640 mg) and the above (R)-triflate compound (978 mg), and (–)-BL-V8-C10 (171 mg, yield: 27%) and (–)-epi-BL-V8-C10 (151 mg, yield: 24%) were obtained in similar manners to those of Example 1 from the above compound (1.01 g). The (–)-BL-V8-C10 was optically purified by preparing an ester compound using N-tosyl-L-valine. The (–)-epi-BL-V8-C10 was not optically purified by a similar procedure and had the optical purity of 80% ee.

(–)-BL-V8-C10: colorless oil, $[\alpha]_D^{22}$=–237.9° (c=0.66, $CHCl_3$)

(–)-epi-BL-V8-C10: colorless oil, $[\alpha]_D^{22}$=–33.2° (c=0.37,$CHCl_3$)

In a similar manner, a hydroxybenzyl ester compound was obtained as colorless oil (1.96 g, yield: 34%) from (S)-n-decanylglycine (5.75 g): $[\alpha]_D^{22}$=–12.3° (c=1.04, $CHCl_3$).

From this compound (900 mg), (S)-triflate compound was obtained as colorless oil (991 mg, yield: 77%): $[\alpha]_D^{22}$=–31.5° (c=1.28,$CHCl_3$).

According to the method of Example 1, colorless oil was obtained (651 mg, yield:74%) from the above-obtained methylaniline compound (mp 102°–104° C., $C_{15}H_{24}N_2O_3$, 435 mg) and the above-obtained triflate compound (770 mg). From this compound (651 mg), (+)-BL-V8-C10 (124 mg, yield: 30%) and (+)-epi-BL-V8-C10 (110 mg, yield: 27%) were obtained in similar manners to those of Example 1. The (+)-BL-V8-C10 was optically purified as in the case of (–)-BL-V8-C10. The (+)-epi-BL-V8-C10 had the optical purity of 80%ee.

(+)-BL-V8-C10: colorless oil, $[\alpha]_D^{22}$=+239.7° (c=0.66, $CHCl_3$)

(+)-epi-BL-V8-C10: colorless oil, $[\alpha]_D^{22}$=+32.3° (c=0.37,$CHCl_3$)

Example 11

Preparation of (±)-BL-V8-23T 2,5-Dichloro-2,5-dimethylhexane (67.5 g, 0.369 mol) was dissolved in dry toluene (200 ml), and then $AlCl_3$ (4.05 g, 30.4 mmol) was crushed up and added portionwise to the solution. After being left for 2 hours, the reaction mixture was poured into ice/5% HCl and the mixture was extracted with hexane. The organic layer was washed each twice with water, aqueous sodium hydrogen carbonate, and then with water, dried over $MgSO_4$, and the solvent was removed by evaporation. The residue was distilled to give 5,6,7,8-tetrahydro-2,5,5,8,8-pentamethylnaphthalene (70.42 g, yield: 90%). bp 100° C. (solidified at room temperature).

The above compound (60 g) was dissolved in acetic acid (240 ml) and cooled over ice-bath. Nitric acid (30 ml, 2 eq.) and sulfuric acid (63 ml, 4 eq.) was added to the solution over 20 minutes while the temperature of the reaction mixture was maintained at 10°–15° C. The reaction mixture was warmed to room temperature and stirred for 4 hours. Chilled water (500 ml) was added to the mixture under ice-cooling, and the pale yellow mass precipitated were collected by filtration and washed sufficiently with water. The resulting precipitates were dissolved in methylene chloride, washed successively with a 1N aqueous NaOH and water, dried over $MgSO_4$, and then the solvent was evaporated. The residue was recrystallized from ethanol to give 3-nitro compound as colorless foliates (45.55 g, yield: 62.1%). mp 150.5°–152° C.

Elemental Analysis: $C_{15}H_{21}NO_2$ Calculated N: 5.66% C: 72.84% H: 8.56% Found N: 5.86% C: 73.08% H: 8.56%

The above-obtained compound (42 g) was dissolved in $CCl_4$ (400 ml) and N-bromosuccinimide (33.3 g, 1.10 eq.) was added and suspended in the solution. After the further addition of AIBN (560 mg, 0.02 eq.), the mixture was refluxed. After 1 hour, AIBN (560 mg, 0.02 eq.) was added to the mixture and reflux was continued for 3 hours. The reaction mixture was cooled, and after the addition of n-hexane (600 ml), the mixture was filtered to remove insolubles and the filtrate was concentrated. A small amount of n-hexane was added to the residue and the mixture was cooled for solidification. The resulting solid was recrystallized from n-pentane and twice from n-hexane to give a benzyl bromide compound as pale yellow needles (23.2 g, yield:41.9%). mp 87.5°–89° C.

Elemental Analysis: $C_{15}H_{20}NO_2Br$ Calculated N: 4.29% C: 55.23% H: 6.18% Found N: 4.16% C: 55.23% H: 6.29%

NaH (2.8 g, purity: 60%, 1 eq.) was washed with n-hexane, and then DMF 50 ml was added and a suspension was prepared. A solution of malonic acid diethylacetoamide (15.3 g, 1 eq.) in DMF (25 ml) was added to the suspension. Then, the above-obtained benzyl bromide compound (23 g) was dissolved in DMF (25 ml) and added to the mixture at 0° C. and stirring was continued at room temperature for 4 hours. The reaction mixture was poured into iced water and the mixture was extracted with methylene chloride, and after dryness over $MgSO_4$, the solvent was removed by evaporation. The residue was recrystallized from methylene chloride/hexane to give a malonic acid diethylacetoamide adduct as pale yellow prisms (23.37 g, yield: 71.9%). mp 132°–133° C.

Elemental Analysis: $C_{24}H_{34}N_2O_7$ Calculated N: 6.06% C: 62.32% H: 7.41% Found N: 6.16% C: 62.16% H: 7.40%

The above compound (22.7 g) was refluxed in a 10% aqueous NaOH (100 ml, 5 eq.) for 75 minutes and then ice-cooled. The reaction mixture was acidified by adding concentrated hydrochloric acid, and the mixture was sufficiently cooled and the precipitates were collected by filtration. The resulting precipitates were washed with a small volume of water and dried at 80° C. for 2 hours under reduced pressure. The resulting des-ester compound was suspended in water (55 ml) and refluxed for 3 hours. Then, the precipitates were collected by filtration, washed with chilled water, and dried at 80°–90° C. for 4 hours under reduced pressure to give a decarbonated compound (12.4 g). $SOCl_2$ (10 ml) was slowly added to anhydrous ethanol (60 ml) at −10° C. and stirring was continued for additional 10 minutes at −10°C. The above decarbonated compound (12.4 g) was added to the solution, and stirring was continued at room temperature for 1 hour and at 60 for 3 hours. The ethanol was removed by evaporation at 60 under reduced pressure, and after the addition of sodium carbonate and water, the mixture was extracted with methylene chloride. The organic layer was concentrated and the resulting residue was dissolved in ethanol, and after the treatment with activated charcoal, the solvent was removed by evaporation. The residue was purified using silica gel column chromatography (solvent: methylene chloride/ethyl acetate=15:1) and recrystallized from methylene chloride/n-hexane to give an ethyl ester compound as pale yellow foliates (10.01 g, yield: 52.2%). mp 184.5°–186° C.

Elemental Analysis: $C_{21}H_{30}N_2O_5$ Calculated N: 7.17% C: 64.60% H: 7.74% Found N: 7.04% C: 64.43% H: 7.62%

The above compound (9.87 g) was dissolved in ethanol saturated with hydrochloric acid (110 ml) and the solution was refluxed for 48 hours. Hydrochloric acid/ethanol was removed by evaporation under reduced pressure, and ethanol (50 ml) was added and evaporated, and then again ethanol (50 ml) was added and evaporated. The residue was dissolved in water and the solution was made basic by adding sodium hydrogen carbonate, and then the mixture was extracted with methylene chloride. After dryness over $MgSO_4$, the solvent was removed by evaporation and the residue was recrystallized from n-hexane to give an amino-deprotected compound as pale yellow needles (7.44 g, yield: 84.5%). mp 86°–87° C.

Elemental Analysis: $C_{19}H_{28}N_2O_4$ Calculated N: 8.04% C: 65.49% H: 8.10% Found N: 7.95% C: 65.62% H: 8.31%

The above-obtained amino ester compound (7.35 g) was dissolved in a mixture of dioxane (40 ml) and water (20 ml), and after the addition of sodium hydrogen carbonate (4.44 g, 2.5 eq.), the mixture was stirred. Boc-$N_3$ (6.04 g, 2 equivalents) was added to the reaction mixture and the mixture was stirred at 45°–50° C. for 40 hours. Boc-$N_3$ (3.02 g, 1 eq.) and sodium hydrogen carbonate (2.22 g, 1.25 eq.) were further added and stirring was continued at the same temperature for 24 hours. Then, water (50 ml) was added to the reaction mixture and the mixture was concentrated under reduced pressure to remove the dioxane. Water (50 ml) was added to the residue for solidification of the oily product. The product was collected by filtration, washed sufficiently with water, and then dissolved in methylene chloride. The solution was washed successively with water, 10% aqueous solution of citric acid, and then with water, dried over $MgSO_4$, and the solvent was evaporated. The residue was recrystallized from n-hexane to give N-Boc compound as colorless plates (8.79 g, yield: 92.9%). mp 131°–132° C.

Elemental Analysis: $C_{24}H_{36}N_2O_6$ Calculated N: 6.25% C: 64.26% H: 8.09% Found N: 6.23% C: 64.305 H: 8.16%

The above-obtained compound (8.65 g) was dissolved in THF (70 ml) and stirred at 0° C., and after the addition of $LiBH_4$ (1.0 g) in THF (30 ml), stirring was continued at 0° C. for 1 hour and at 30° C. for 2 hours. Water (200 ml) was carefully added to the reaction mixture and the mixture was extracted with methylene chloride. The organic layer was washed successively with a 10% aqueous citric acid and water, dried over $MgSO_4$, and the solvent was removed by evaporation to give a hydroxymethyl compound in the form of an oil (6.60 g, yield: 84.2%).

The above-obtained compound (3.3 g) was dissolved in ethyl acetate/1% $H_2O$ (500 ml), and after the addition of 10% Pd/C (2.0 g), hydrogen gas was introduced over the reaction mixture under an ambient pressure at room temperature for catalytic hydrogenation. Pd/C was removed by filtration and the filtrate was concentrated. The residue was recrystallized from n-hexane to give an aniline compound as colorless prisms (2.77 g, yield: 90.6%). mp 112.5°–114° C.

Elemental Analysis: $C_{22}H_{36}N_2O_3$ Calculated N: 7.44% C: 70.18% H: 9.64% Found N: 7.28% C: 70.26% H: 9.93%

The above-obtained compound (3.05 g) was dissolved in benzene (40 ml), and after the addition of methyl 2-oxoisovalerate (3.16 g, 3 eq. ), the mixture was subjected to azeotropic reflux for 24 hours under argon atmosphere. The benzene and the methyl 2-oxoisovalerate was evaporated under reduced pressure and the resulting residue was dissolved in THF (40 ml). $NaBH_3$ CN (1.0 g, 2 eq.) was added to the solution and the mixture was left at room temperature for 3 hours. The reaction mixture was concentrated to 10 ml at 40° C. under reduced pressure, and after the addition of 10% aqueous citric acid (100 ml) and methylene chloride (50 ml), the mixture was stirred for 2 hours. This mixture was extracted with methylene chloride, and then the organic layer was dried over $MgSO_4$ and the solvent was evaporated. The residue was purified using silica gel column chromatography (solvent: methylene chloride/ethyl acetate=15:1 ) to give a mixture of an imino compound and an enamine compound. This mixture was dissolved in methanol (300 ml), and after the addition of 10% Pd/of 10% Pd/C (3.05 g), hydrogen gas was introduced at 1 atm at room temperature to carry out catalytic hydrogenation for 5 hours. After removal of Pd/C by filtration, the filtrate was concentrated and the residue was purified using silica gel column chromatography (solvent: methylene chloride/ethyl acetate =12:1) to give a mixture of isomers (2.95 g, yield: 74.2%).

The above-obtained mixture of isomers (2.85 g) was dissolved in methanol (48 ml), and after the addition of 2N potassium hydroxide (14.5 ml, 5 eq.), the mixture was stirred at 60° C. for 1 hour and then methanol was evaporated at 40° C. under reduced pressure. The concentrate was acidified by adding a 10% aqueous citric acid under ice-cooling and the mixture was extracted with ethyl acetate, and then the solvent was evaporated to give a des-ester compound. The des-ester compound was immediately dissolved in $CH_3CN$ (16 ml), and after the addition of N-hydroxysuccinimide (1.34 g, 2 equivalents), the mixture was cooled to 0° C. A solution of DCC (1.80 g, 1.5 eq.) in $CH_3CN$ (6 ml) was added to the solution, and the mixture was left at 0° C. for 1 hours and then at room temperature for 2 hours. The solvent was removed by evaporation and the resulting residue was dissolved in ethyl acetate and the insolubles were removed by filtration. The filtrate was concentrated and the residue was purified using silica gel column chromatography (solvent: methylene chloride/ethyl acetate=40:7) to give a mixture of isomers of activated ester as colorless liquid (2.35 g, yield: 70.5%).

The above mixture (2.30 g) was dissolved in methylene chloride (15 ml) and cooled to 0° C., and after the addition of $CF_3COOH$ (15 ml) and substitution with argon atmosphere, the mixture was left for 1 hour. The solvent was removed by evaporation at room temperature under reduced pressure, and water (50 ml) was added to the residue and then an excess amount of sodium hydrogen carbonate was added. After the addition of ethyl acetate (70 ml), the mixture was refluxed for 1 hour. The ethyl acetate layer was separated and the aqueous layer was extracted with ethyl acetate. The organic layers were combined and dried over $MgSO_4$, and the solvent was evaporated. The residue was purified using silica gel column chromatography (solvent: methylene chloride/ethyl acetate=1:2) to separate two isomers (total yield: 52.7%).

Isomer A: 393 mg, colorless plate, mp 215°–216° C.

Isomer B (epi-compound): 364 mg, colorless plate, mp 265°–268° C.

The above isomer B (epi-compound, 150 mg) was dissolved in methanol (5 ml), and sodium hydrogen carbonate (250 mg) was added to the solution. After the addition of $CH_3I$ (7.5 ml), the mixture was refluxed for 44 hours. After evaporation of methanol and $CH_3I$, water was added to the residue and the mixture was extracted with chloroform. After dryness of the organic layer, the solvent was removed by evaporation and the residue was purified using silica gel column chromatography (solvent: methylene chloride/ethyl acetate=3:2) to give epi-BL-V8-23T as colorless needles (132.4 mg, yield: 84.7%). mp 247°–248° C.

Elemental Analysis: $C_{23}H_{36}N_2O_2$ Calculated N: 7.52% C: 74.15% H: 9.74%

Found N: 7.52% C: 74.08% H: 9.71%

The above isomer A (200 mg) was dissolved in methanol (7 ml) and sodium hydrogen carbonate (300 mg) was added to the solution. After the addition of $CH_3$ I (11 ml), the mixture was refluxed for 48 hours. After evaporation of methanol and $CH_3I$, water was added to the residue and the mixture was extracted with chloroform. The organic layer was dried and then concentrated, and the resulting residue was purified using silica gel column chromatography (solvent: methylene chloride/ethyl acetate=2:1) to give BL-V8-23T as colorless needles (135.0 mg, yield: 65.0%). mp 255°–256° C.

Elemental Analysis: $C_{23}H_{36}N_2O_2$ Calculated N: 7.52% C: 74.15% H: 9.74% Found N: 7.41% C: 74.43% H: 9.70%

Experiments

Antiretroviral activities and cytotoxicities of the benzolactam compounds of the present invention obtained in Examples were tested.

(1) Antiviral activity (A) A human T-cell strain MOLT-4 clone 8, persistently infected with HIV (HIV-$1_{IIIB}$ strain), was cultured in RPMI-1640 medium supplemented with 10% fetal bovine serum. The culture supernatant was then filtered and and stored at −80° C. after a measurement of viral titer. Each of test compounds was diluted with the above culture medium so as to be a predetermined concentration, and 50 μl of the solution was added to each of wells of a 96-well microtiter plate. Then, after the addition of each 100 μl of MT-4 cell suspension ($3.5 \times 10^4$ cells) to the well, the above-prepared HIV-containing supernatant was diluted with the above medium and 50μl of the dilution (60 plaque forming units) was added to each well.

(B) After incubation of the 96-well microtiter plate in a $CO_2$-incubator at 37° C. for 5 days, 30 μl of MTT [3-(4,5-dimethylthiazole-2-yl)-2,5-diphenyltetrazorium bromide, 5 mg/ml, PBS] was added to each well and incubation was continued for 1 hour.

Cells having survived reduced MTT to precipitate formazan. 150 μl of culture supernatant was removed from each well and 150 μl of a solubilizing solution (10% Triton X-100 and isopropanol supplemented with 0.4% (V/V) HCl) was added to each well and the plate was shaken by using a plate mixer to dissolve the formazan. The dissolved formazan was measured by O.D. at 540 nm and the results were compared with referenced control. $EC_{50}$ (μg/ml) was defined as a concentration of the compound that achieved 50% inhibition of cytotoxicity by the virus. DMSO was used as a solvent and the tested concentrations were 0.0001–10 μg/ml.

(2) Cytotoxicity

Cytotoxicities of the test compounds against the MT-4 cells were measured in the same manner as step (A) of the above-described antiviral activity test, provided that 50 μl of the culture medium was added to each well instead of the HIV-containing supernatant (virus solution), which was followed by the same treatment as step (B). $CC_{50}$ (μg/ml) was defined as a concentration of test compound inducing 50% cytotoxicity. The results are summarized in table 2 set out below.

TABLE 2

| Compound tested | $CC_{50}$ (μg/ml) | $EC_{50}$ (μg/ml) |
| --- | --- | --- |
| BL-V8 | 10 | 0.1–1 |
| epi-BL-V8 | 10 | 2.5–5 |
| BL-V8-23T | 1–10 | $>CC_{50}$ |
| epi-BL-V8-23T | 1–10 | $>CC_{50}$ |
| (±)-BL-V8-310 | 1 | 0.001–0.01 |
| (±)-epi-BL-V8-310 | 1 | 0.13 |
| (−)-BL-V8-310 | 5–10 | 0.003 |
| (+)-BL-V8-310 | 5–10 | 0.05–0.1 |
| (−)-epi-BL-V8-310 | 2.5–5 | 0.16 |
| (+)-epi-BL-V8-310 | 5–10 | 0.1 |
| BL-V9 | >10 | >10 |
| epi-BL-V9 | >10 | >10 |
| BL-V9-310 | 10 | 2.5–5 |
| epi-BL-V9-310 | 5–10 | 0.3 |
| BL-V10 | >10 | >10 |
| epi-BL-V10 | >10 | >10 |

INDUSTRIAL APPLICABILITY

The benzolactam derivatives of the present invention have antiretroviral activities and reduced side effects such as cytotoxicity. Therefore, they are useful for therapeutic and preventive treatments of retrovirus infectious diseases such as AIDS.

What is claimed is:

1. A benzolactam represented by the following formula (I):

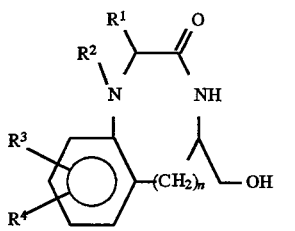

wherein n represents an integer of from 1 to 3; $R^1$ represents a straight- or branched-chain alkyl group having 1 to 12 carbon atoms or a benzyl group or a phenethyl group; $R^2$ represents a straight- or branched-chain alkyl group having 1 to 12 carbon atoms; $R^3$ and $R^4$ independently represent a hydrogen atom or a straight- or branched-chain alkyl group having 1 to 12 carbon atoms, and when $R^3$ and $R^4$ are adjacent each other on the phenyl group, they may be combined to form a cycloalkyl ring having 5 to 7 carbon atoms together with 2 carbon atoms of the phenyl group to which $R^3$ and $R^4$ bind.

2. The benzolactam according to claim 1, wherein $R^3$ and $R^4$ form the cycloalkyl ring, and wherein the cycloalkyl ring is substituted with at least one lower alkyl group.

3. The benzolactam according to claim 1, wherein n is 1 or 2; $R^1$ represents a functional group selected from the group consisting of isopropyl group, isobutyl group, t-butyl group, n-octyl group, n-nonyl group, n-decanyl group, and benzyl group; $R^2$ represents a functional group selected from the group consisting of methyl group, n-octyl group, n-nonyl group, and n-decanyl group; and $R^3$ and $R^4$ independently represent a hydrogen atom or a straight- or branched-chain alkyl group containing 1 to 12 carbon atoms or they form a 6-membered cycloalkyl ring.

4. The benzolactam according to claim 3, wherein $R^3$ and $R^4$ form the 6-membered cycloalkyl ring, and wherein the cycloalkyl ring is substituted with at least one lower alkyl group.

5. The benzolactam according to claim 1, wherein $R^1$ represents a functional group selected from the group consisting of isopropyl group, isobutyl group, and t-butyl group; $R^2$ represents a methyl group; and $R^3$ and $R^4$ independently represent a hydrogen atom or a straight-chain alkyl group containing 10 carbon atoms or they form a 6-membered cycloalkyl ring.

6. The benzolactam according to claim 5, wherein $R^3$ and $R^4$ form the 6-membered cycloalkyl ring, and wherein the cycloalkyl ring is substituted with at least one methyl group.

7. An anti-retroviral agent comprising as an active ingredient a benzolactam represented by the following formula (I):

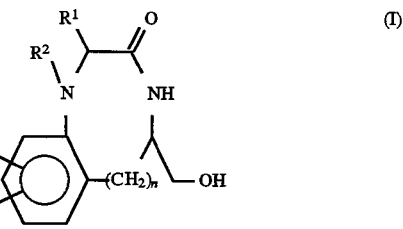

wherein n represents an integer of from 1 to 3; $R^1$ represents a straight- or branched-chain alkyl group having 1 to 12 carbon atoms or a benzyl group or a phenethyl group; $R^2$ represents a straight- or branched-chain alkyl group having 1 to 12 carbon atoms; $R^3$ and $R^4$ independently represent a hydrogen atom or a straight- or branched-chain alkyl group having 1 to 12 carbon atoms, and when $R^3$ and $R^4$ are adjacent each other on the phenyl group, they may be combined to form a cycloalkyl ring having 5 to 7 carbon atoms together with 2 carbon atoms of the phenyl group to which $R^3$ and $R^4$ bind.

8. The anti-retroviral agent according to claim 7, wherein $R^3$ and $R^4$ are combined to form the cycloalkyl ring, and wherein the cycloalkyl ring has at least one lower alkyl group.

9. The anti-retroviral agent according to claim 7, wherein the retrovirus is a human acquired immunodeficiency virus.

* * * * *